United States Patent
Ai et al.

(10) Patent No.: US 10,202,584 B2
(45) Date of Patent: Feb. 12, 2019

(54) RED-SHIFTED LUCIFERASE-LUCIFERIN PAIRS FOR ENHANCED BIOLUMINESCENCE

(71) Applicant: The Regents of the University of California, Oakland, CA (US)

(72) Inventors: Huiwang Ai, Charlottesville, VA (US); Hsien-Wei Yeh, Charlottesville, VA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/694,238

(22) Filed: Sep. 1, 2017

(65) Prior Publication Data

US 2018/0057801 A1    Mar. 1, 2018

Related U.S. Application Data

(60) Provisional application No. 62/382,255, filed on Sep. 1, 2016.

(51) Int. Cl.
| | |
|---|---|
| *C12N 9/02* | (2006.01) |
| *C12Q 1/66* | (2006.01) |
| *A61K 49/00* | (2006.01) |
| *C07D 487/04* | (2006.01) |
| *G01N 33/542* | (2006.01) |

(52) U.S. Cl.
CPC ........ *C12N 9/0069* (2013.01); *A61K 49/0013* (2013.01); *A61K 49/0045* (2013.01); *C07D 487/04* (2013.01); *C12Q 1/66* (2013.01); *C12Y 113/12007* (2013.01); *G01N 33/542* (2013.01); *C07K 2319/00* (2013.01); *G01N 2333/90241* (2013.01)

(58) Field of Classification Search
CPC ............ A61K 49/0013; A61K 49/0045; C07D 487/04; C07K 2319/00; C12N 9/0069; C12Q 1/66; C12Y 113/12007; G01N 2333/90241; G01N 33/54
See application file for complete search history.

(56) References Cited

U.S. PATENT DOCUMENTS 8,546,147 B2 * 10/2013 Giuliani ............... C07D 487/04 435/7.72
8,669,103 B2 * 3/2014 Binkowski ........... C07D 487/04 435/325
9,139,836 B2 * 9/2015 Klaubert .............. C07D 487/04

OTHER PUBLICATIONS

Negrin, R.S. & Contag, C.H. Nat. Rev. Immunol. 6, 484-490 (2006).
Arranz, A. & Ripoll, J. Frontiers in pharmacology 6, 189 (2015).
Inglese, J. et al. Nat. Chem. Biol. 3, 466-479 (2007).
Saito, K. et al. Nat. Commun. 3, 1262 (2012).
Hall, M.P. et al. ACS Chem. Biol. 7, 1848-1857 (2012).
Stacer, A.C. et al. Mol. Imaging 12: 1-13 (2013).
Adams, S.T., Jr. & Miller, S.C. Curr. Opin. Chem. Biol. 21c, 112-120 (2014).
Evans, M.S. et al. Nat. Methods 11, 393-395 (2014).
Kuchimaru, T. et al. Nat. Commun. 7, 11856 (2016). Inouye, S. et al. Biochem. Biophys. Res. Commun. 437, 23-28 (2013).
Inouye, S. & Shimomura, O. Biochem. Biophys. Res. Commun. 233, 349-353 (1997).
Wu, C., Nakamura, H., Murai, A. & Shirnomura, O. Tetrahedron Lett. 42, 2997-3000 (2001).
Inouye, S. et al. Biochem. Biophys. Res. Commun. 437, 23-28 (2013).
Jiang, T., Du, L. & Li, M. Photochem. Photobiol. Sci. 15, 466-480 (2015).
Nishihara, R. et al. Chem. Commun. 51, 391-394 (2015).
Inouye, S., Sato, J., Sahara-Miura, Y., Yoshida, S. & Hosoya, T. Biochem. Biophys. Res. Commun. 445, 157-162 (2014).
Omabechi, Y. et al. Biochem. Biophys. Res. Commun. 470, 88-93 (2016).
Chu, J. et al. Nat. Biotechnol. 34, 760-767 (2016).
Suzuki, K. et al. Nat. Commun. 7, 13718 (2016).
Dixon, A.S. et al. ACS Chem. Biol. 11, 400-408 (2016).
Yang, J. et al. Nat. Commun. 7, 13268 (2016).
Inouye, S. et al., FEBS Lett. Sep. 8, 2000;481(1):19-25.
Giuliani, G. et al. Tetrahedron Lett. 53, 5114-5118 (2012).
Yuan, M.-L., Jiang, T.-Y., Du, L.-P. & Li, M.-Y. Chin. Chem. Lett. 27, 550-554 (2016).
Sun, Y.Q. et al. Angew. Chem. Int. Ed. Engl. 51, 7634-7636 (2012).
Yamashita, Y., Ono, K., Tamura, M. & Tanaka, S. Tetrahedron 53, 10169-10178 (1997).
Conley, N.R., Dragulescu-Andrasi, A., Rao, J. & Moerner, W.E. Angew. Chem. Int. Ed. Engl. 51, 3350-3353 (2012).
Adamczyk, M. et al. Tetrahedron 59, 8129-8142 (2003).
Schindelin, J. et al. Nat. Methods 9, 676-682 (2012).
Ando, Y. et al. Photochem. Photobiol. 83, 1205-1210 (2007).
Loening, A.M., Dragulescu-Andrasi, A. & Gambhir, S.S. Nat. Methods 7, 5-6 (2010).
Ando, Y. et al. Nat Photon 2, 44-47 (2008).
Liu, F., Song, Y. & Liu, D. Gene Ther. 6, 1258-1266 (1999).

* cited by examiner

*Primary Examiner* — Marcela M Cordero Garcia
(74) *Attorney, Agent, or Firm* — Brooks Kushman P.C.

(57) ABSTRACT

A bioluminescent protein is provided that includes a substituted luciferase polypeptide having amino acid substitutions at positions 21 and 166, and with one or more additional amino acid substitutions at positions 3, 16, 20, 29, 30, 71, 87, 114, and 144, compared to the parent polypeptide. Also provided is a luciferin that has a selenium-containing group at position C8 of an imidazopyrazine backbone, and methods of making the luciferin. In addition, nucleic acids encoding the bioluminescent protein, cells expressing the bioluminescent protein, and reactions between the bioluminescent protein and luciferin substrates are also provided. Fusions between the substituted luciferase polypeptide and a fluorescent protein are also provided for bioluminescence resonance energy transfer based reporters.

20 Claims, 26 Drawing Sheets
(8 of 26 Drawing Sheet(s) Filed in Color)
Specification includes a Sequence Listing.

```
NanoLuc   1  M V F T L E D F V G D W R Q T A G Y N L D Q V L E Q G G V S S L F Q N L G V S V T P I  41
teLuc        M V F T L E D F V G D W R Q T A G Y N L D Q V L E Q G G V S S L F Q N L G V S V T P I
yeLuc0.8     M V F T L E D F V G D W R Q T A G Y N L G Q V L E Q G G V S S L F Q N L G V S V T P I
yeLuc        M V L T L E D F V G D W R Q T D G Y N L G Q A L E Q G G V T L L F Q N L G V S V T P I NanoLuc  42  Q R I V L S G E N G L K I D I H V I - - - P Y E G L S G D Q M G Q I E K I F K V V Y P V D  81
teLuc        Q R I V L S G E N G L K I D I H V I - - - P Y E G L S G D Q M G Q I E K I F K V V Y P V D
yeLuc0.8     Q R I V L S G E N G L K I D I H V I - - - P Y E G L S G D Q M G Q I E K I F K V V Y P V D
yeLuc        Q R I V L S G E N G L K I D I H V I - - - P Y E G L S G D R M G Q I E K I F K V V Y P V D NanoLuc  82  D H H F K V I L H Y G T L V I D G V T P N M I D Y F G R P Y E G I A V F D G K K I T V  126
teLuc        N H H F K V I L H Y G T L V I D G V T P N M I D Y F G R P Y E G I A V F D G K K I T V
yeLuc0.8     D H H F K V I L H Y G T L V I D G V T P N M I D Y F G R P Y E G I A V F D G K K I T V
yeLuc        D H H F K V I L H Y G T L V I D G V T P N M I D Y F G Q P Y E G I A V F D G K K I T V NanoLuc 127  T G T L W N G N K I I D E R L I N P D G S L L F R V T I N G V T G W R L C E R I L A -  166
teLuc        T G T L W N G N K I I D E R L I N P D G S L L F R V T I N G V T G W R L C E R I L A -
yeLuc0.8     T G T L W N G N K I I D E R L I N P D G S L L F R V T I N G V T G W R L H E R I L A -
yeLuc        T G T L W N G N K I I D E R R I N P D G S L L F R V T I N G V T G W R L S E R I L A -
```

FIG. 4

SEQUENCE LISTING

```
<160> NUMBER OF SEQ ID NOS: 40

<210> SEQ ID NO 1
<211> LENGTH: 171
<212> TYPE: PRT
<213> ORGANISM: Artificial Sequence
<220> FEATURE:
<223> OTHER INFORMATION: Engineered mutant of Oplophorus gracilirostris
      polypeptide
```

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170

<210> SEQ ID NO 2
<211> LENGTH: 171
<212> TYPE: PRT
<213> ORGANISM: Artificial Sequence
<220> FEATURE:
<223> OTHER INFORMATION: Engineered mutant of Oplophorus gracilirostris
      polypeptide

<400> SEQUENCE: 2

Met Val Phe Thr Leu Glu Asp Phe Val Gly Asp Trp Arg Gln Thr Ala
1               5                   10                  15

Gly Tyr Asn Leu Ser Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asn His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu His Glu Arg Ile Leu Ala
                165                 170

```
<210> SEQ ID NO 3
<211> LENGTH: 171
<212> TYPE: PRT
<213> ORGANISM: Artificial Sequence
<220> FEATURE:
<223> OTHER INFORMATION: Engineered mutant of Oplophorus gracilirostris
      polypeptide

<400> SEQUENCE: 3
```

| Met | Val | Phe | Thr | Leu | Glu | Asp | Phe | Val | Gly | Asp | Trp | Arg | Gln | Thr | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Tyr | Asn | Gln | Ala | Gln | Val | Leu | Glu | Gln | Gly | Gly | Val | Thr | Ser | Leu |
|     |     |     | 20  |     |     |     |     | 25  |     |     |     |     | 30  |     |     |

| Phe | Gln | Asn | Leu | Gly | Val | Ser | Val | Thr | Pro | Ile | Gln | Arg | Ile | Val | Leu |
|     |     |     | 35  |     |     |     |     | 40  |     |     |     |     | 45  |     |     |

| Ser | Gly | Glu | Asn | Gly | Leu | Lys | Ile | Asp | Ile | His | Val | Ile | Ile | Pro | Tyr |
| 50  |     |     |     |     | 55  |     |     |     |     | 60  |     |     |     |     |     |

| Glu | Gly | Leu | Ser | Gly | Asp | Gln | Met | Gly | Gln | Ile | Glu | Lys | Ile | Phe | Lys |
| 65  |     |     |     |     | 70  |     |     |     |     | 75  |     |     |     |     | 80  |

| Val | Val | Tyr | Pro | Val | Asp | Asp | His | His | Phe | Lys | Val | Ile | Leu | His | Tyr |
|     |     |     |     | 85  |     |     |     |     | 90  |     |     |     |     | 95  |     |

| Gly | Thr | Leu | Val | Ile | Asp | Gly | Val | Thr | Pro | Asn | Met | Ile | Asp | Tyr | Phe |
|     |     |     |     | 100 |     |     |     |     | 105 |     |     |     |     | 110 |     |

| Gly | Arg | Pro | Tyr | Glu | Gly | Ile | Ala | Val | Phe | Asp | Gly | Lys | Lys | Ile | Thr |
|     |     |     | 115 |     |     |     |     | 120 |     |     |     |     | 125 |     |     |

| Val | Thr | Gly | Thr | Leu | Trp | Asn | Gly | Asn | Lys | Ile | Ile | Asp | Glu | Arg | Leu |
|     |     |     | 130 |     |     |     |     | 135 |     |     |     |     | 140 |     |     |

| Ile | Asn | Pro | Asp | Gly | Ser | Leu | Leu | Phe | Arg | Val | Thr | Ile | Asn | Gly | Val |
| 145 |     |     |     |     | 150 |     |     |     |     | 155 |     |     |     |     | 160 |

| Thr | Gly | Trp | Arg | Leu | Ser | Glu | Arg | Ile | Leu | Ala |
|     |     |     |     | 165 |     |     |     |     | 170 |     |

```
<210> SEQ ID NO 4
<211> LENGTH: 171
<212> TYPE: PRT
<213> ORGANISM: Artificial Sequence
<220> FEATURE:
<223> OTHER INFORMATION: Engineered mutant of Oplophorus gracilirostris
      polypeptide

<400> SEQUENCE: 4
```

| Met | Val | Leu | Thr | Leu | Glu | Asp | Phe | Val | Gly | Asp | Trp | Arg | Gln | Thr | Asp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Tyr | Asn | Gln | Ala | Gln | Val | Leu | Glu | Gln | Gly | Gly | Leu | Thr | Ser | Leu |
|     |     |     | 20  |     |     |     |     | 25  |     |     |     |     | 30  |     |     |

| Phe | Gln | Asn | Leu | Gly | Val | Ser | Val | Thr | Pro | Ile | Gln | Arg | Ile | Val | Leu |
|     |     |     | 35  |     |     |     |     | 40  |     |     |     |     | 45  |     |     |

| Ser | Gly | Glu | Asn | Gly | Leu | Lys | Ile | Asp | Ile | His | Val | Ile | Ile | Pro | Tyr |
| 50  |     |     |     |     | 55  |     |     |     |     | 60  |     |     |     |     |     |

| Glu | Gly | Leu | Ser | Gly | Asp | Arg | Met | Gly | Gln | Ile | Glu | Lys | Ile | Phe | Lys |
| 65  |     |     |     |     | 70  |     |     |     |     | 75  |     |     |     |     | 80  |

| Val | Val | Tyr | Pro | Val | Asp | Asp | His | His | Phe | Lys | Val | Ile | Leu | His | Tyr |
|     |     |     |     | 85  |     |     |     |     | 90  |     |     |     |     | 95  |     |

| Gly | Thr | Leu | Val | Ile | Asp | Gly | Val | Thr | Pro | Asn | Met | Ile | Asp | Tyr | Phe |
|     |     |     |     | 100 |     |     |     |     | 105 |     |     |     |     | 110 |     |

| Gly | Gln | Pro | Tyr | Glu | Gly | Ile | Ala | Val | Phe | Asp | Gly | Lys | Lys | Ile | Thr |
|     |     |     | 115 |     |     |     |     | 120 |     |     |     |     | 125 |     |     |

```
Val Thr Gly Thr Leu Trp Asn Gly Asn Lys Ile Ile Asp Glu Arg Arg
        130                 135                 140

Ile Asn Pro Asp Gly Ser Leu Leu Phe Arg Val Thr Ile Asn Gly Val
145                 150                 155                 160

Thr Gly Trp Arg Leu Ser Glu Arg Ile Leu Ala
                165                 170
```

<210> SEQ ID NO 5
<211> LENGTH: 40
<212> TYPE: DNA
<213> ORGANISM: Artificial Sequence
<220> FEATURE:
<223> OTHER INFORMATION: PCR primer

<400> SEQUENCE: 5
gcaactcgag catggtcttc acactcgaag atttcgttgg          40

<210> SEQ ID NO 6
<211> LENGTH: 37
<212> TYPE: DNA
<213> ORGANISM: Artificial Sequence
<220> FEATURE:
<223> OTHER INFORMATION: PCR primer

<400> SEQUENCE: 6
ttgccaagct tacgccagaa tgcgttcgca cagccgc             37

<210> SEQ ID NO 7
<211> LENGTH: 57
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 7
ccgatccaaa ggnnkgtcct gagcggtgaa aatgggctga agnnkgacat ccatgtc    57

<210> SEQ ID NO 8
<211> LENGTH: 57
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 8
gacatggatg tcmnncttca gcccattttc accgctcagg acmnncctttt ggatcgg   57

<210> SEQ ID NO 9
<211> LENGTH: 39
<212> TYPE: DNA
<213> ORGANISM: Artificial Sequence

```
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t

<400> SEQUENCE: 9
tggaacggca acaaaattnn kgacgagcgc ctgatcaac                                   39

<210> SEQ ID NO 10
<211> LENGTH: 39
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (20)..(21)
<223> OTHER INFORMATION: n is a, c, g, or t

<400> SEQUENCE: 10
gttgatcagg cgctcgtcmn naattttgtt gccgttcca                                   39

<210> SEQ ID NO 11
<211> LENGTH: 48
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t

<400> SEQUENCE: 11
cagacagccg gctacaacnn knnkcaagtc cttgaacagg gaggtgtg                         48

<210> SEQ ID NO 12
<211> LENGTH: 48
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 12
cacacctccc tgttcaagga cttgmnnmnn gttgtagccg gctgtctg                         48

<210> SEQ ID NO 13
<211> LENGTH: 54
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (29)..(30)
<223> OTHER INFORMATION: n is a, c, g, or t
```

<220> FEATURE:
<221> NAME/KEY: misc_feature
<222> LOCATION: (35)..(36)
<223> OTHER INFORMATION: n is a, c, g, or t

<400> SEQUENCE: 13
ttgccaagct tacgccagaa tgcgttcmnn cagmnnccag ccggtcactc cgtt        54

<210> SEQ ID NO 14
<211> LENGTH: 48
<212> TYPE: DNA
<213> ORGANISM: Artificial Sequence
<220> FEATURE:
<223> OTHER INFORMATION: PCR primer

<400> SEQUENCE: 14
aataaagctt gccgccacca tggtcttcac actcgaagat ttcgttgg              48

<210> SEQ ID NO 15
<211> LENGTH: 31
<212> TYPE: DNA
<213> ORGANISM: Artificial Sequence
<220> FEATURE:
<223> OTHER INFORMATION: PCR primer

<400> SEQUENCE: 15
taatctcgag ttacgccaga atgcgttcgc a                                31

<210> SEQ ID NO 16
<211> LENGTH: 31
<212> TYPE: DNA
<213> ORGANISM: Artificial Sequence
<220> FEATURE:
<223> OTHER INFORMATION: PCR primer

<400> SEQUENCE: 16
taatctcgag ttacgccaga atgcgttcat g                                31

<210> SEQ ID NO 17
<211> LENGTH: 31
<212> TYPE: DNA
<213> ORGANISM: Artificial Sequence
<220> FEATURE:
<223> OTHER INFORMATION: PCR primer

<400> SEQUENCE: 17
taatctcgag ttacgccaga atgcgttcac t                                31

<210> SEQ ID NO 18
<211> LENGTH: 49
<212> TYPE: DNA
<213> ORGANISM: Artificial Sequence
<220> FEATURE:
<223> OTHER INFORMATION: PCR primer

<400> SEQUENCE: 18
attataaagc ttgccgccac catggaagac gccaaaaaca taaagaaag             49

<210> SEQ ID NO 19
<211> LENGTH: 40
<212> TYPE: DNA
<213> ORGANISM: Artificial Sequence
<220> FEATURE:
<223> OTHER INFORMATION: PCR primer

<400> SEQUENCE: 19
ttattctcga gttacaattt ggactttccg cccttcttgg          40

<210> SEQ ID NO 20
<211> LENGTH: 42
<212> TYPE: DNA
<213> ORGANISM: Artificial Sequence
<220> FEATURE:
<223> OTHER INFORMATION: PCR primer

<400> SEQUENCE: 20
attataaagc ttgccgccac catggtgagc aagggcgagg ag          42

<210> SEQ ID NO 21
<211> LENGTH: 32
<212> TYPE: DNA
<213> ORGANISM: Artificial Sequence
<220> FEATURE:
<223> OTHER INFORMATION: PCR primer

<400> SEQUENCE: 21
ttattctcga gttacttgta cagctcgtcc at          32

<210> SEQ ID NO 22
<211> LENGTH: 27
<212> TYPE: DNA
<213> ORGANISM: Artificial Sequence
<220> FEATURE:
<223> OTHER INFORMATION: PCR primer

<400> SEQUENCE: 22
ggctacaact tgagtcaagt ccttgaa          27

<210> SEQ ID NO 23
<211> LENGTH: 27
<212> TYPE: DNA
<213> ORGANISM: Artificial Sequence
<220> FEATURE:
<223> OTHER INFORMATION: PCR primer

<400> SEQUENCE: 23
ttcaaggact tgactcaagt tgtagcc          27

<210> SEQ ID NO 24
<211> LENGTH: 25
<212> TYPE: DNA
<213> ORGANISM: Artificial Sequence
<220> FEATURE:
<223> OTHER INFORMATION: PCR primer

<400> SEQUENCE: 24
taccctgtgg ataatcatca cttta          25

<210> SEQ ID NO 25
<211> LENGTH: 25
<212> TYPE: DNA
<213> ORGANISM: Artificial Sequence
<220> FEATURE:
<223> OTHER INFORMATION: PCR primer

<400> SEQUENCE: 25
taaagtgatg attatccaca gggta          25

```
<210> SEQ ID NO 26
<211> LENGTH: 33
<212> TYPE: DNA
<213> ORGANISM: Artificial Sequence
<220> FEATURE:
<223> OTHER INFORMATION: PCR primer

<400> SEQUENCE: 26
tgaccggctg gcgtctgcat gaacgcattc tgg                             33

<210> SEQ ID NO 27
<211> LENGTH: 33
<212> TYPE: DNA
<213> ORGANISM: Artificial Sequence
<220> FEATURE:
<223> OTHER INFORMATION: PCR primer

<400> SEQUENCE: 27
ccagaatgcg ttcatgcaga cgccagccgg tca                             33

<210> SEQ ID NO 28
<211> LENGTH: 32
<212> TYPE: DNA
<213> ORGANISM: Artificial Sequence
<220> FEATURE:
<223> OTHER INFORMATION: PCR primer

<400> SEQUENCE: 28
ataactcgag catggtgagc aagggcgagg ag                              32

<210> SEQ ID NO 29
<211> LENGTH: 30
<212> TYPE: DNA
<213> ORGANISM: Artificial Sequence
<220> FEATURE:
<223> OTHER INFORMATION: PCR primer

<400> SEQUENCE: 29
ttgccaagct tacttgtaca gctcgtccat                                 30

<210> SEQ ID NO 30
<211> LENGTH: 47
<212> TYPE: DNA
<213> ORGANISM: Artificial Sequence
<220> FEATURE:
<223> OTHER INFORMATION: PCR primer

<400> SEQUENCE: 30 tgagttttg ttcgccggag cccgccagaa tgcgttcgca cagccgc                47

<210> SEQ ID NO 31
<211> LENGTH: 47
<212> TYPE: DNA
<213> ORGANISM: Artificial Sequence
<220> FEATURE:
<223> OTHER INFORMATION: PCR primer

<400> SEQUENCE: 31 tgagttttg ttcgccggag cccgccagaa tgcgttcatg cagacgc                47

<210> SEQ ID NO 32
<211> LENGTH: 47
<212> TYPE: DNA
<213> ORGANISM: Artificial Sequence
<220> FEATURE:
<223> OTHER INFORMATION: PCR primer
```

<400> SEQUENCE: 32
tgagtttttg ttcgccggag cccgccagaa tgcgttcact cagacgc        47

<210> SEQ ID NO 33
<211> LENGTH: 48
<212> TYPE: DNA
<213> ORGANISM: Artificial Sequence
<220> FEATURE:
<223> OTHER INFORMATION: PCR primer

<400> SEQUENCE: 33
tgagtttttg ttcgccggag cccaatttgg actttccgcc cttcttgg       48

<210> SEQ ID NO 34
<211> LENGTH: 47
<212> TYPE: DNA
<213> ORGANISM: Artificial Sequence
<220> FEATURE:
<223> OTHER INFORMATION: PCR primer

<400> SEQUENCE: 34
tgagtttttg ttcgccggag cccttgtaca gctcgtccat gcctccg        47

<210> SEQ ID NO 35
<211> LENGTH: 53
<212> TYPE: DNA
<213> ORGANISM: Artificial Sequence
<220> FEATURE:
<223> OTHER INFORMATION: PCR primer

<400> SEQUENCE: 35
taattctcga gttacagatc ctcttctgag atgagttttt gttcgccgga gcc    53

<210> SEQ ID NO 36
<211> LENGTH: 60
<212> TYPE: DNA
<213> ORGANISM: Artificial Sequence
<220> FEATURE:
<223> OTHER INFORMATION: PCR primer

<400> SEQUENCE: 36
gcaggctgga gacgtggagg agaaccctgg acctatggaa gacgccaaaa acataaagaa    60

<210> SEQ ID NO 37
<211> LENGTH: 60
<212> TYPE: DNA
<213> ORGANISM: Artificial Sequence
<220> FEATURE:
<223> OTHER INFORMATION: PCR primer

<400> SEQUENCE: 37
ccagggttct cctccacgtc tccagcctgc ttcagcaggc tgaagttagt agctccgctt    60

<210> SEQ ID NO 38
<211> LENGTH: 51
<212> TYPE: DNA
<213> ORGANISM: Artificial Sequence
<220> FEATURE:
<223> OTHER INFORMATION: PCR primer

<400> SEQUENCE: 38
aggctgaagt tagtagctcc gcttcccgcc agaatgcgtt catgcagacg c       51

```
<210> SEQ ID NO 39
<211> LENGTH: 51
<212> TYPE: DNA
<213> ORGANISM: Artificial Sequence
<220> FEATURE:
<223> OTHER INFORMATION: PCR primer

<400> SEQUENCE: 39
aggctgaagt tagtagctcc gcttcccgcc agaatgcgtt cgcacagccg c           51

<210> SEQ ID NO 40
<211> LENGTH: 22
<212> TYPE: PRT
<213> ORGANISM: Porcine teschovirus

<400> SEQUENCE: 40

Gly Ser Gly Ala Thr Asn Phe Ser Leu Leu Lys Gln Ala Gly Asp Val
 1               5                  10                  15

Glu Glu Asn Pro Gly Pro
            20
```

RED-SHIFTED LUCIFERASE-LUCIFERIN PAIRS FOR ENHANCED BIOLUMINESCENCE

CROSS-REFERENCE TO RELATED APPLICATIONS

This application claims the benefit of Provisional Patent Application No. 62/382,255, filed on Sep. 1, 2016, which is incorporated by reference herein.

REFERENCE TO SEQUENCE LISTING

A Sequence Listing is submitted electronically via EFS-Web as an ASCII formatted text file with the name "1279614 SeqList"; the file was created on Aug. 25, 2017, is 13.9 kilobytes in size, and is incorporated herein by reference in its entirety.

BACKGROUND

Field of the Invention

The invention relates to compositions and methods for bioluminescence.

Related Art

There is enormous interest in harnessing bioluminescence for ultrasensitive bioassays, drug screening, and optical imaging (1-3). For example, luciferases have been broadly utilized to develop assays for screening chemical or genomic libraries. Moreover, luciferases have also been frequently utilized to label cancer cells so that, subsequently, cancer metastasis and the responses of cancer progression to drugs and drug candidates can be investigated. The photon fluxes of bioluminescent reporters are determined by the quantum efficiencies and catalytic rates of bioluminescence reactions. The slow catalysis of common luciferases often results in bioluminescence emission several orders of magnitude lower than that of fluorescence (4). A recent advancement was the development of NanoLuc luciferase, which, when paired with a synthetic furimazine substrate (see FIG. 3), generates intense blue bioluminescence much higher than other popular reporters (5). However, the in vivo performance of NanoLuc, particularly in deep tissues, is poor since photons shorter than 600 nm interact strongly with mammalian tissues (6). Because a significant portion of Firefly luciferase (FLuc) emission is longer than 600 nm, FLuc/D-luciferin remains among the top choices for deep-tissue bioluminescence imaging (BLI) (7). Although both FLuc and D-luciferin have recently been engineered for longer wavelength emission, this desirable spectral shift is often offset by a substantially reduced total intensity (7). Only a very few examples, such as the D-luciferin analogues CycLuc1 and AkaLumine-HCl (8,9), can modestly enhance FLuc bioluminescence at limited substrate concentration ranges.

It can be reasoned that an improved bioluminescence reporter may be derived by red-shifting the emission of NanoLuc. Several early studies reported red-shifted CTZ analogs for Oplophorus luciferase, the ancestor of NanoLuc (10,11); however, their intensities were low and it is unclear whether the spectral shift could be extended to NanoLuc. Recent studies directly tested NanoLuc with several synthetic CTZ analogs but no red-shift was noted (12-14).

SUMMARY

The development of novel luciferase-luciferin pairs is described based on synthetic coelenterazine (CTZ) analogs with their correspondingly re-engineered luciferases. Because of its enhanced photon flux and red-shifted emission, one such pair shows superior sensitivity over other common bioluminescence reporters, both in vitro and in vivo. This new luciferase was adapted into a bioluminescence resonance energy transfer (BRET)-based Antares reporter and the resultant Antares2 further enhanced bioluminescence from deep tissues. Thus, novel luciferase-luciferin pairs based on other CTZ analogs and correspondingly re-engineered NanoLuc mutants are provided for substantially brighter and red-shifted bioluminescence.

In one aspect, a bioluminescent protein is provided. The bioluminescent protein includes a luciferase polypeptide or an amino acid sequence variant of the luciferase polypeptide, with the sequence variant retaining enzymatic ability to act on a luciferin substrate. In some embodiments, the sequence variant can be a substituted luciferase polypeptide that includes the amino acid sequence set forth in SEQ ID NO: 1 but with amino acid substitutions occurring at positions corresponding to positions 21 and 166 of SEQ ID NO: 1. The substituted luciferase polypeptide also includes one or more amino acid substitutions at one or more positions corresponding to positions 3, 16, 20, 29, 30, 71, 87, 114, and 144 of SEQ ID NO: 1.

In some versions of the bioluminescent protein: a) the substituted luciferase polypeptide is substituted at positions corresponding to position 87, positions 20 and 30, or positions 3, 16, 20, 29, 30, 71, 114, and 144, of SEQ ID NO: 1; b) the substituted luciferase polypeptide includes or has the amino acid sequence of SEQ ID NO: 2, 3 or 4; c) the bioluminescent protein further includes a fluorescent protein connected to the luciferase polypeptide, such as the substituted luciferase polypeptide; d) in some versions that include a fluorescent protein, one copy of the fluorescent protein is fused to the N-terminus of the substituted luciferase polypeptide and another copy of the fluorescent protein is fused to the C-terminus of the substituted luciferase polypeptide; e) in some versions that include a fluorescent protein, the fluorescent protein is connected to the substituted luciferase polypeptide so as to allow bioluminescence resonant energy transfer (BRET) between the substituted luciferase polypeptide and the fluorescent protein; f) in some versions that include a fluorescent protein, the substituted luciferase polypeptide comprises or has the amino acid sequence of SEQ ID NO: 2, 3 or 4; or g) any combination of a)-f).

In another aspect, a compound is provided having the formula

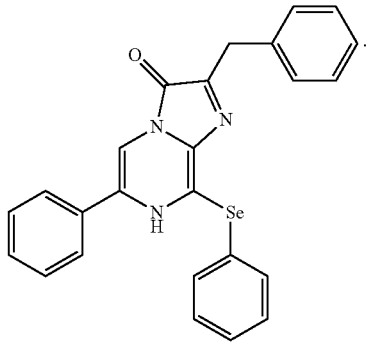 [SMILES: O=c1c(Cc2ccccc2)nc2c([Se]c3ccccc3)[nH]c(-c3ccccc3)cn1-2]

In a further aspect, a method of preparing an analog of coelenterazine is provided, where coelenterazine includes an imidazopyrazine backbone. The chemical name of coelenterazine is 6-(4-hydroxyphenyl)-2-[(4-hydroxyphenyl)methyl]-8-(phenylmethyl)-7H-imidazo[1,2-a]pyrazin-3-one. In general, the method includes modifying position C8 of the imidazopyrazine backbone. In some versions, the method comprises including a selenium-containing group at position C8 of the imidazopyrazine backbone.

In some versions of the method, the preparing is carried out according to the following Scheme I:

Scheme 1

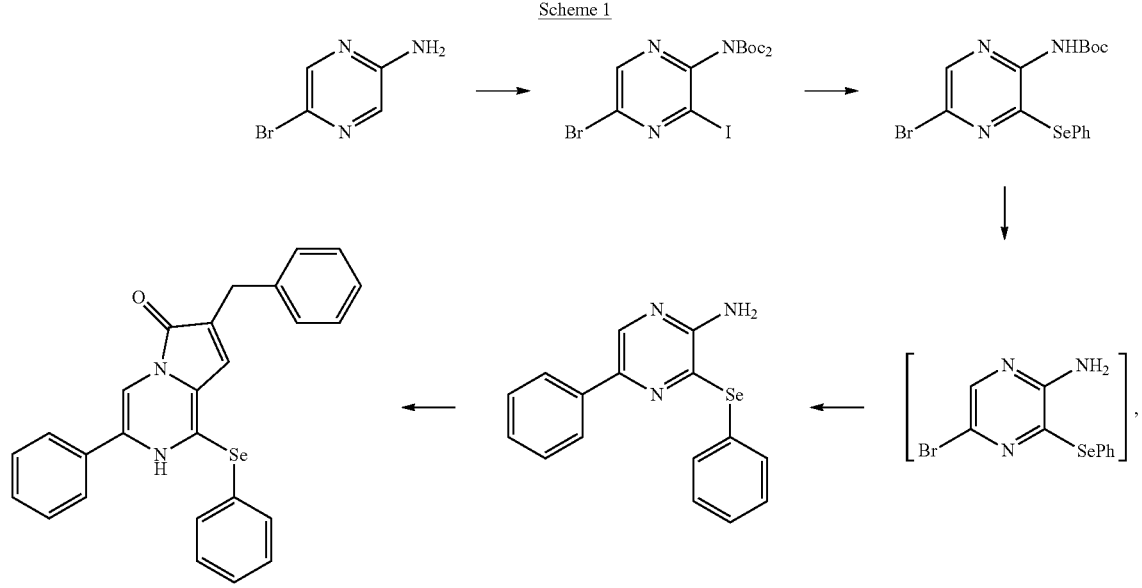

with the method including:

reacting 2-amino-5-bromopyrazine with N-iodosuccinimide to produce a reaction product, and reacting the reaction product with di-tert-butyl dicarbonate to produce di-tert-butyl (5-bromo-3-iodopyrazin-2-yl)carbamate;

reacting the di-tert-butyl (5-bromo-3-iodopyrazin-2-yl) carbamate with diphenyl diselenide to produce tert-butyl (5-bromo-3-(phenylselanyl)pyrazin-2-yl)carbamate;

removing the Boc group from the tert-butyl (5-bromo-3-(phenylselanyl)pyrazin-2-yl)carbamate to give 5-bromo-3-(phenylselanyl)pyrazin-2-amine, and then substituting a phenyl group for the bromo group of 5-bromo-3-(phenylselanyl)pyrazin-2-amine to produce 5-phenyl-3-(phenylselanyl)pyrazin-2-amine;

and reacting the 5-phenyl-3-(phenylselanyl)pyrazin-2-amine with 1,1-diethoxy-3-phenylacetone to produce the analog selenoterazine (chemical name is 2-benzyl-6-phenyl-8-(phenylselanyl)imidazo[1,2-a]pyrazin-3 (7H)-one).

In another aspect, a combination is provided. The combination includes the bioluminescent protein described herein and a luciferin. In some versions: a) the substituted luciferase polypeptide of the bioluminescent protein includes or has the amino acid sequence of SEQ ID NO: 2, 3 or 4; b) the luciferin is one or a combination of the following compounds:

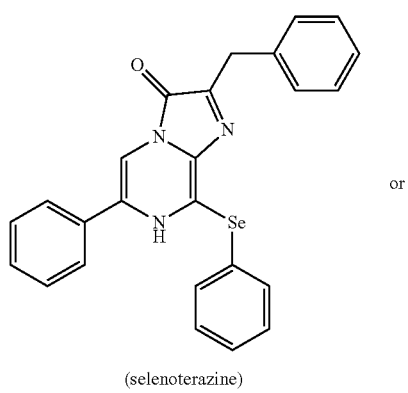

(selenoterazine)

or

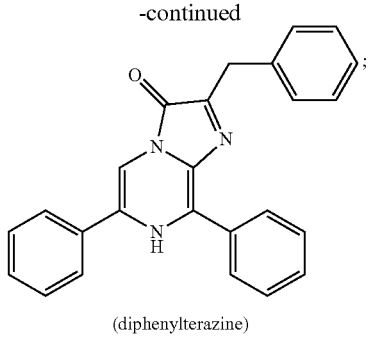

(diphenylterazine)

or c) any combination of a) and b).

In another aspect, a nucleic acid encoding a bioluminescent protein described herein is provided. Further, a vector encoding the nucleic acid, including an expression vector that includes the nucleic acid functionally connected to a promoter and other control sequences, as needed, for expression of the bioluminescent protein, is provided. In addition, a cell containing the expression vector and expressing the bioluminescent protein is provided.

In a further aspect, a method of producing luminescence is provided. The method includes reacting a luciferin with the bioluminescent protein described herein. In some versions of the method: a) the substituted luciferase polypeptide of the bioluminescent protein comprises or has the amino acid sequence of SEQ ID NO: 2, 3 or 4; b) the luciferin is selenoterazine and/or diphenylterazine; c) the bioluminescent protein further includes a fluorescent protein connected to the luciferase polypeptide, such as the substituted luciferase polypeptide, so as to allow BRET activity between the substituted luciferase polypeptide and the fluorescent protein; d) or any combination of a) c). Embodiments that include a fluorescent protein can be used as reporters in BRET assays.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is now made to the following descriptions taken in conjunction with the accompanying drawings, in which:

FIG. 3 is a panel of chemical structures of coelenterazine (CTZ) (3a) and CTZ analogs (3b-3e). The C2, C6 and C8 positions of the imidazopyrazine backbone of coelenterazine is shown in 3a.

FIG. 4 is an amino acid sequence alignment between the NanoLuc polypeptide (SEQ ID NO: 1) and NanoLuc mutants teLuc (SEQ ID NO: 2), yeLuc0.8 (SEQ ID NO: 3) and yeLuc (SEQ ID NO: 4) described herein. The mutations in teLuc, yeLuc0.8 and yeLuc are highlighted. Residues in this figure are numbered according to Protein Date Bank (PDB) ID 5B0U.

DETAILED DESCRIPTION

Figure 1:
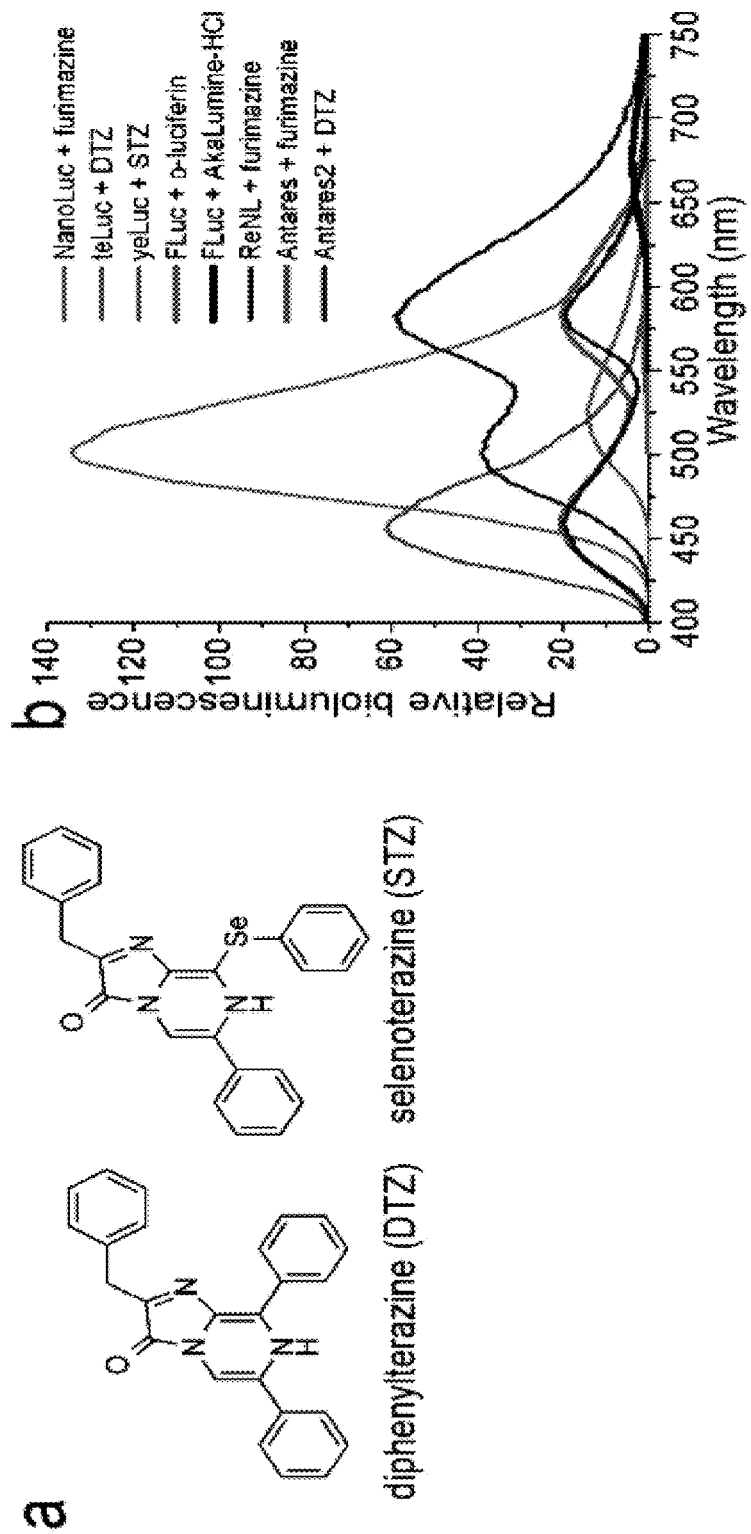
FIG. 1 is a panel of results for bioluminescent reporters based on synthetic substrates and re-engineered luciferases. (1a) Chemical structures of diphenylterazine (DTZ) and selenoterazine (STZ). (1b) Bioluminescence emission of purified luciferases (1 nM) with their corresponding luciferin substrates (30 µM). The spectra were normalized to peak emission of FLuc/D-luciferin. (1c-1f) Representative pseudocolored images (1c,1e) and quantifications (1d,1f) of luciferase-expressing HEK 293T cells in the presence of various luciferins. Images were acquired without a filter (1c) or with a 695±25 nm NIR emission filter (1e). Panels 2d and 2f are quantification results for Panels 2c and 2e, respectively. All values were normalized to the intensities of FLuc/D-luciferin (50 µM) under the same imaging conditions. Data are shown as mean and s.d. of three independent experiments.
Figure 1:
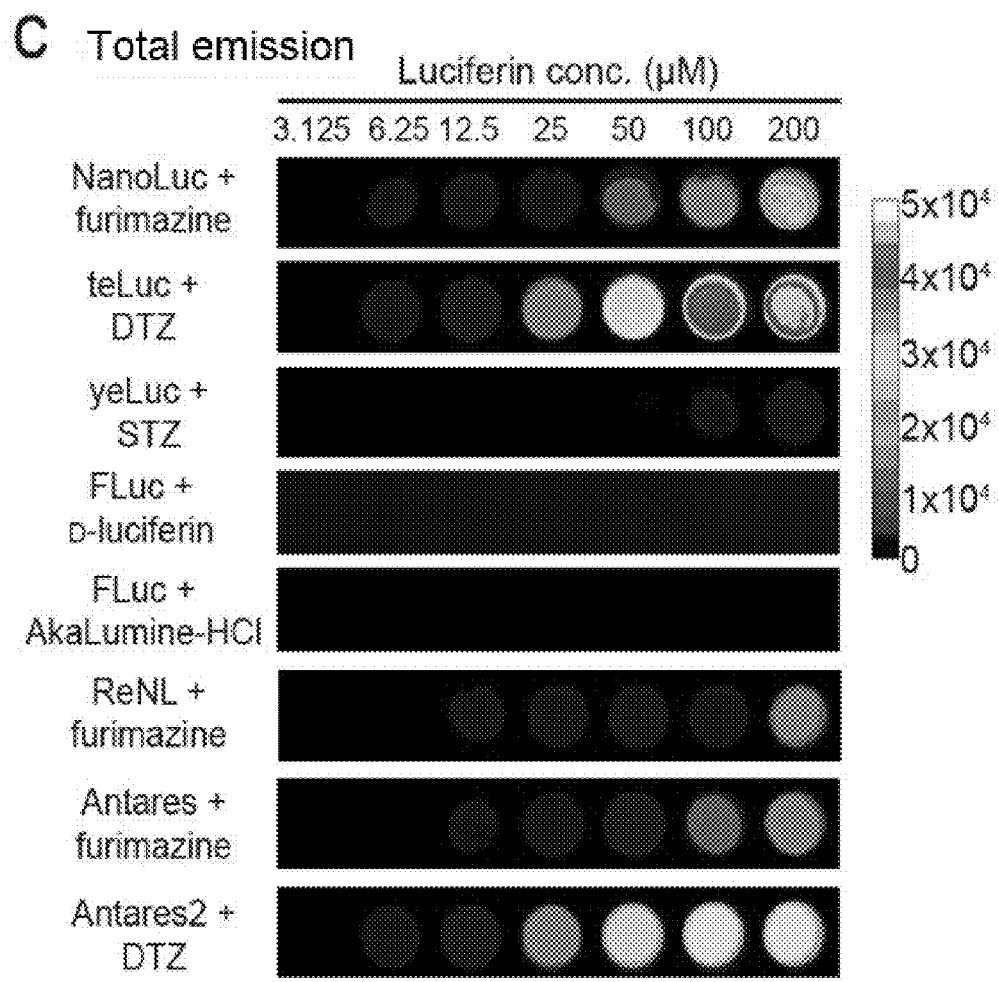
Figure 1:
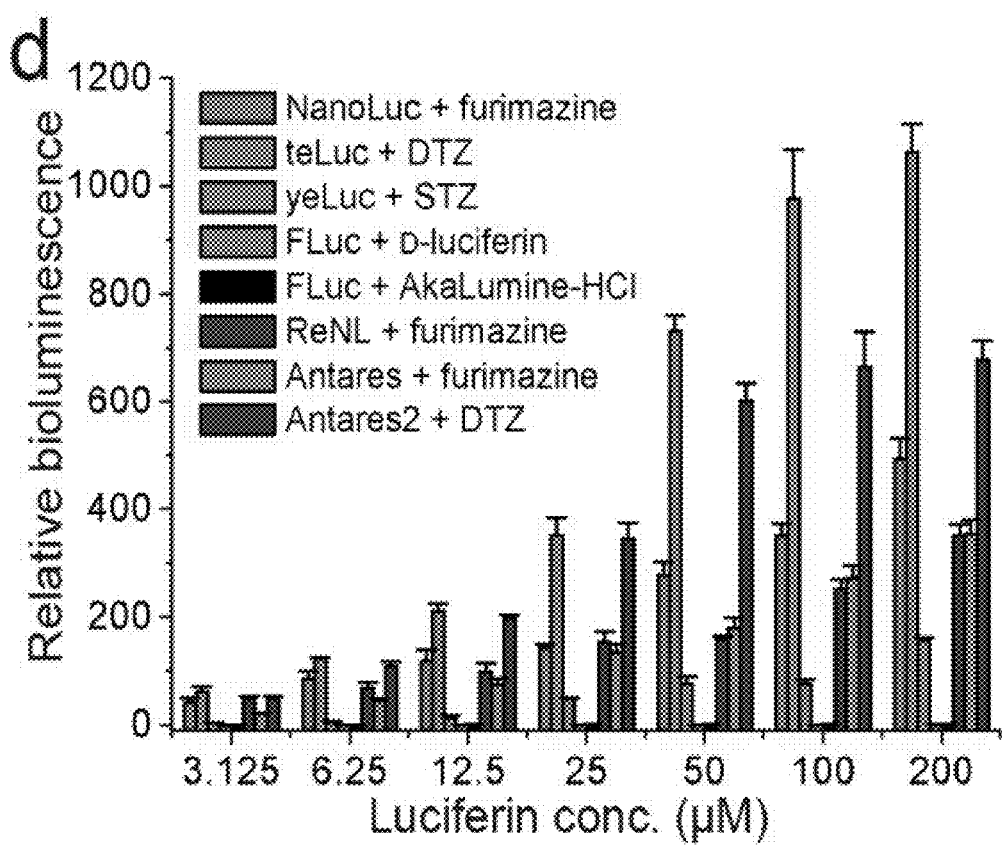
Figure 1:
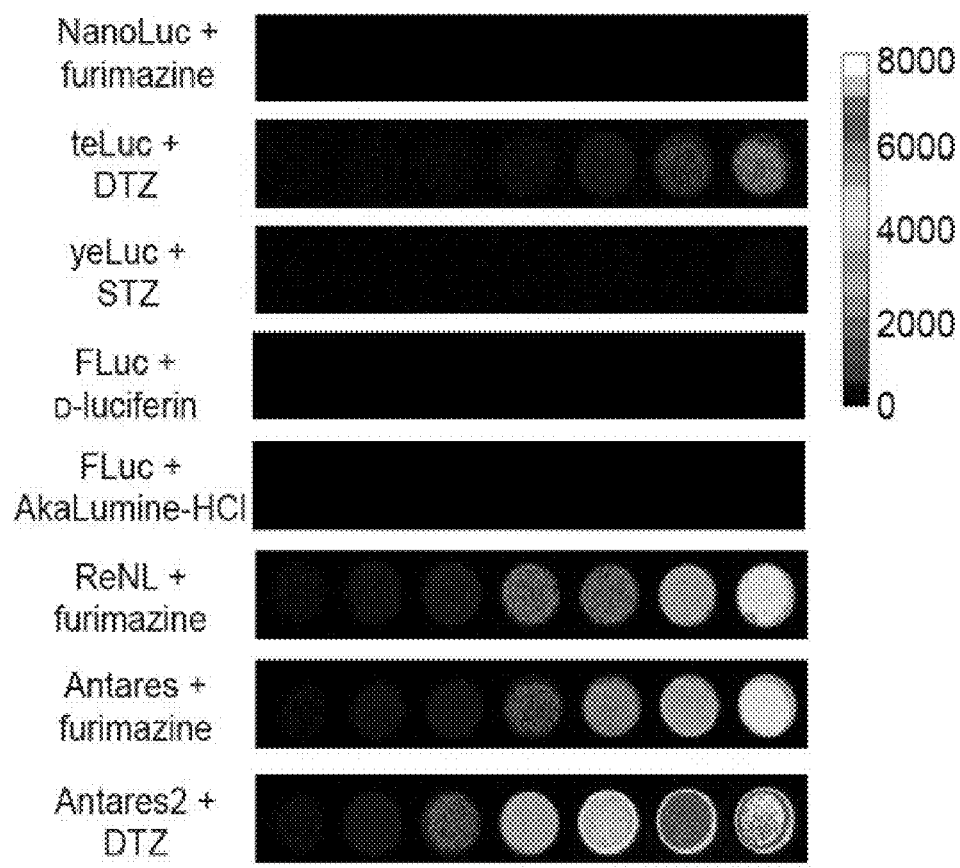
Figure 1:
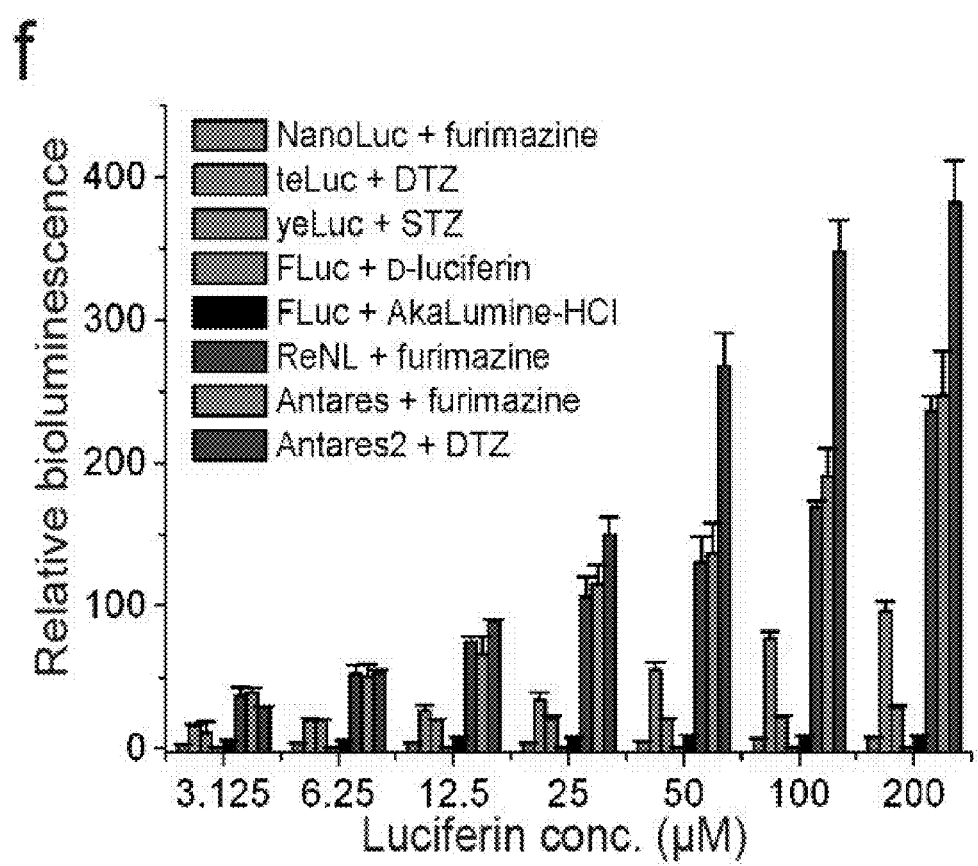

In one aspect, a bioluminescent protein is provided that includes a substituted luciferase polypeptide or other amino acid sequence variants of a luciferase polypeptide. In some embodiments, the substituted luciferase polypeptide is based on the NanoLuc polypeptide. Amino acid sequence variants can be substitutional, insertional or deletion variants. Deletion variants lack one or more residues of the native protein that are not essential for function. For example, a common type of deletion variant is one lacking secretory signal sequences or signal sequences directing a protein to bind to a particular part of a cell. Insertional mutants typically involve the addition of material at a non-terminal point in the polypeptide. This may include the insertion of functional domain or simply a single residue. Terminal additions such as fusion proteins are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. The substitution at a position can be made with any of the twenty amino acids typically found in proteins, although in some embodiments, substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

A sequence comparison can be performed, for example, using the Basic Local Alignment Search Tool (BLAST; located on the World Wide Web at blast.ncbi.nlm.nih.gov/Blast.cgi). In comparing sequences, a segment of comparison between one protein and another may be about 100% of the amino acids of the length being compared, or about 95%, about 85%, or about 80% of the amino acids of the length being compared. The length of comparison may be at least about 20, 30, 40, 50, 55, 60, 65, 70, or 75 amino acids, or more. Relative to an original polypeptide, a variant polypeptide can have about 70% to about 80% identity; about 80% to about 90% identify, about 90% to about 99% identity, about 95% to about 99% identify, or at least 70% identity, at least 80% identify, at least 90% identify, or at least 95% identify, to the original polypeptide.

A specialized kind of insertional variant is the fusion protein. This molecule generally has all or a substantial portion of the native molecule, linked at the N- or C-terminus, to all or a portion of a second polypeptide. For example, fusions typically employ leader tables from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

In some embodiments, the bioluminescent protein comprises a fusion protein of a substituted luciferase polypeptide and a fluorescent protein. The fluorescent protein can be connected to the N- or C-terminus of the substituted luciferase polypeptide, and multiple copies of the fluorescent protein can be attached to the substituted luciferase polypeptide. In some embodiments, one copy of the fluorescent protein is connected to the N-terminus of the substituted luciferase polypeptide, and a second copy of the fluorescent protein is connected to the C-terminus of the substituted luciferase polypeptide.

In some embodiments, substantially pure proteins or polypeptides of at least about 70, 75, 80, 85, 90% homogeneity are provided, with 92, 95, 98 to 99% or more homogeneity in some cases. In some embodiments, an isolated protein or polypeptide is provided.

NanoLuc luciferase was engineered by a commercial entity from a small, 19 kDa-domain of the luciferase cloned from the deep sea shrimp Oplophorus gracirostris. The work was built on the work of Shimomura and co-workers, who cloned the cDNA and identified the small catalytic domain (21). NanoLuc has now been utilized to study gene regulation and cell signaling, monitor protein stability, examine protein-protein or protein-ligand interaction, develop BRET-based biosensors, and image NanoLuc-labeled targets in vitro and in vivo.

In some embodiments, a luciferin is the substrate for a luciferase. The luciferin can be naturally occurring or synthetic, and can be an analog of a naturally occurring or synthetic luciferin. Examples of luciferins include, but are not limited to, coelenterazine, selenoterazine, diphenylterazine, furimazine, 6-pi-OH-CTZ, or a combination thereof.

Standard recombinant methods can be developed, including design of recombinant nucleic acids encoding constructs. See, e.g., Thompson D. A. Cell and Molecular Biology Manual 2011. Expression vectors, e.g., with promoters operably linked to coding regions, can be devised. Cells comprising the vectors are provided, including both prokaryote cells and eukaryote cells. Examples of prokaryotic cells for cloning and expression of recombinant polypeptides include, but are not limited to, *E. coli, Salmonella, Shigella, Streptococcus, Mycobacterium*, and *Pseudomonas*. Examples of eukaryotic cells for expression of recombinant polypeptides include, but are not limited to, HEK 293T, HeLa, and generally other established cell lines, and primary cells derived from mammalian and human tissues. Compatible expression methodologies can also be developed for the luciferase polypeptides described herein. The gene sequences for teLuc, yeLuc, and Antares2 have been deposited to GenBank under the accession numbers KX963378, KX963379, and KY474379, respectively, which are incorporated by reference herein.

Typically, a polynucleotide that encodes the polypeptide of interest is placed under the control of a promoter that is functional in the desired host cell. An extremely wide variety of promoters is well known, and can be used in expression vectors of embodiments of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences can incorporate nucleic acids that encode the relevant functional polypeptides for expression in a desired host cell (see, e.g., Ream W and Field K. G. Molecular Biology Techniques. Academic Press. 2012).

Some embodiments comprise a fluorescent protein connected to a luciferase polypeptide, such as a substituted luciferase polypeptide, for use as BRET based reporters. Examples of the fluorescent protein include, but are not limited to, the cyan-excitable orange fluorescent protein CyOFP, the cyan-excitable red fluorescent protein CyRFP, the red fluorescent protein tdTomato, the monomeric fluorescent protein mCherry, the red fluorescent protein mApple, the far-red fluorescent protein mCardinal, the far-red fluorescent protein mMaroon, and monomeric red fluorescent protein Tarps.

In these BRET-based probes, the teLuc luciferase acts as an energy transfer donor and fluorescent proteins act as energy transfer acceptors. When the emission of the luciferase partially overlaps with the absorption of the acceptor, the luciferase-catalyzed biochemical reaction can excite the acceptors, which can emit photons from the excited acceptors. This setup can be utilized to gain red-shifted photons, which improve in vivo bioluminescence imaging. It may also be utilized to build bioluminescent biosensors by fusing the luciferase and fluorescent proteins with sensory protein domains, for example.

The present invention may be better understood by referring to the accompanying examples, which are intended for illustration purposes only and should not in any sense be construed as limiting the scope of the invention.

Example 1

Figure 3:
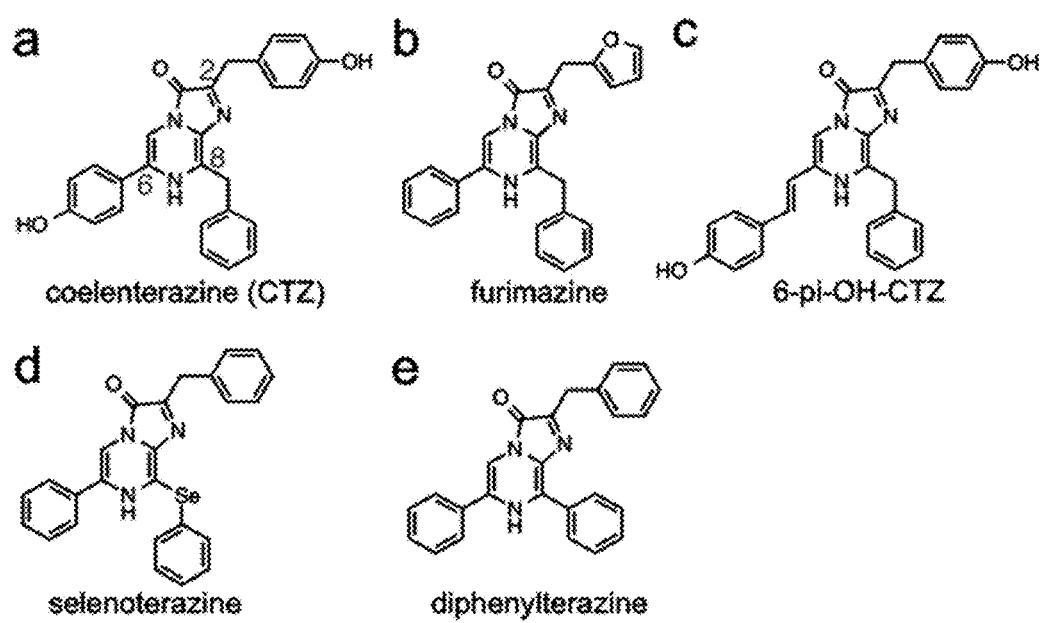

Several CTZ analogs were prepared, including diphenylterazine (DTZ), which extends the CTZ conjugation system through an aromatic ring at C-8, and selenoterazine (STZ), which has a selenium heteroatom at C-8 (FIG. 1a; FIG. 3). When assayed with NanoLuc, DTZ and STZ caused 44- and 71-nm red-shifts from furimazine, respectively, although with reduced brightness (Supplementary Table 1).

Figure 5:
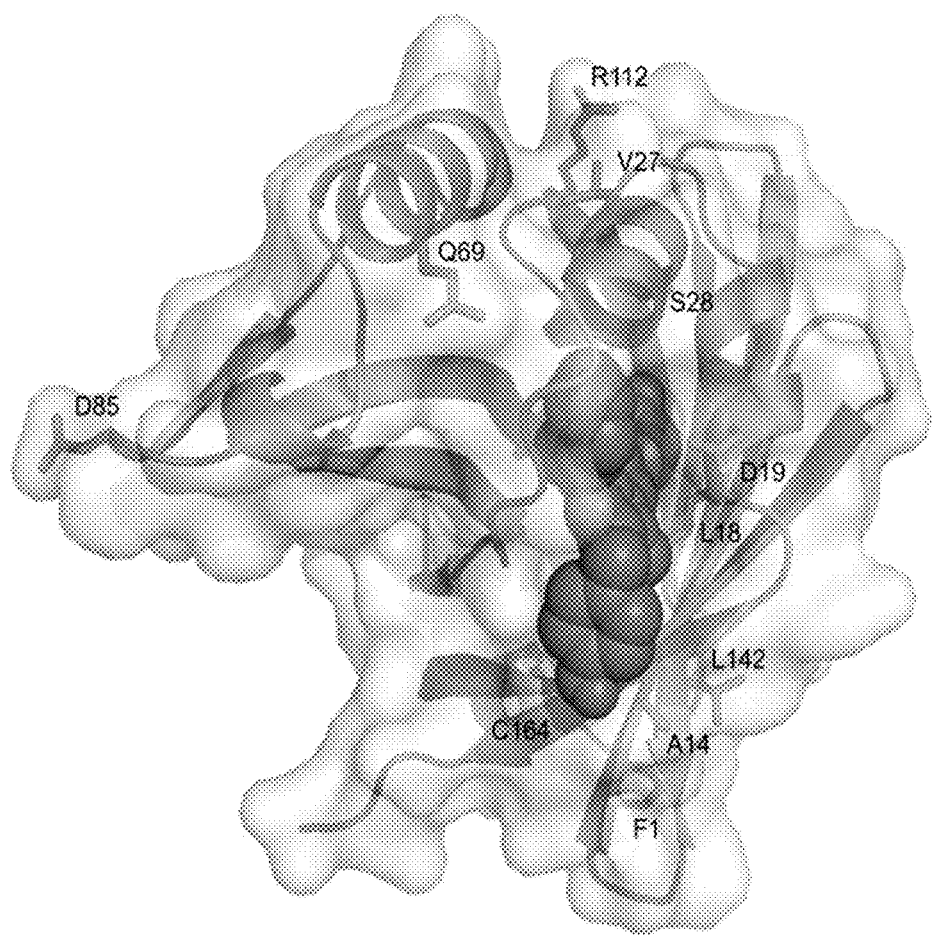
FIG. 5 is an illustration of the binding pocket of NanoLuc and the mutated residues to derive teLuc and yeLuc.
Figure 6:
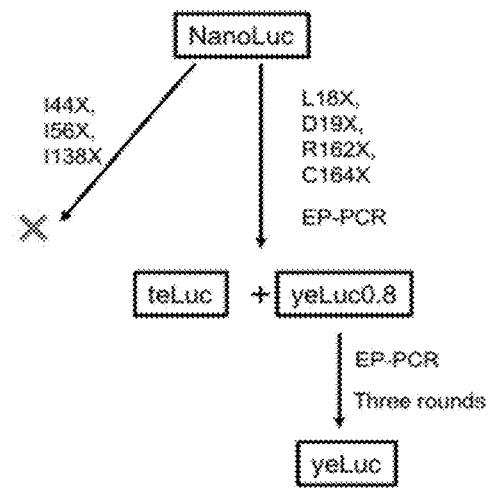
FIG. 6 is a schematic illustration of the process to engineer teLuc and yeLuc.
Figure 7:
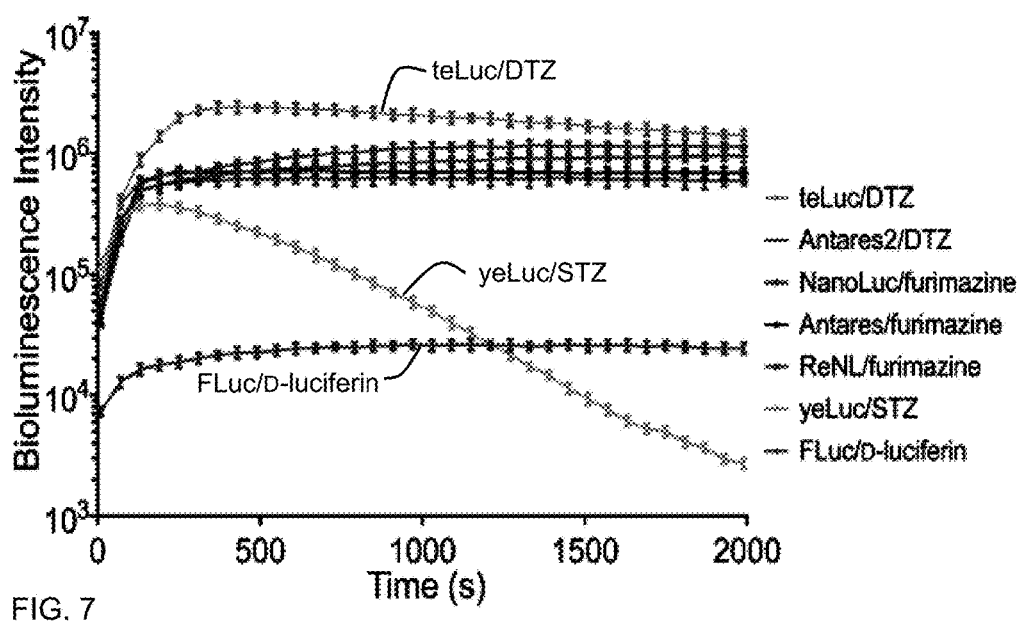
FIG. 7 is a graph of bioluminescence decay kinetics for pure enzymes. The final concentrations of all enzymes and substrates were 100 pM and 30 µM, respectively. Measurements were taken every 60 s after substrate addition. Data are shown as mean and s.d. of three independent experiments.
Figure 8:
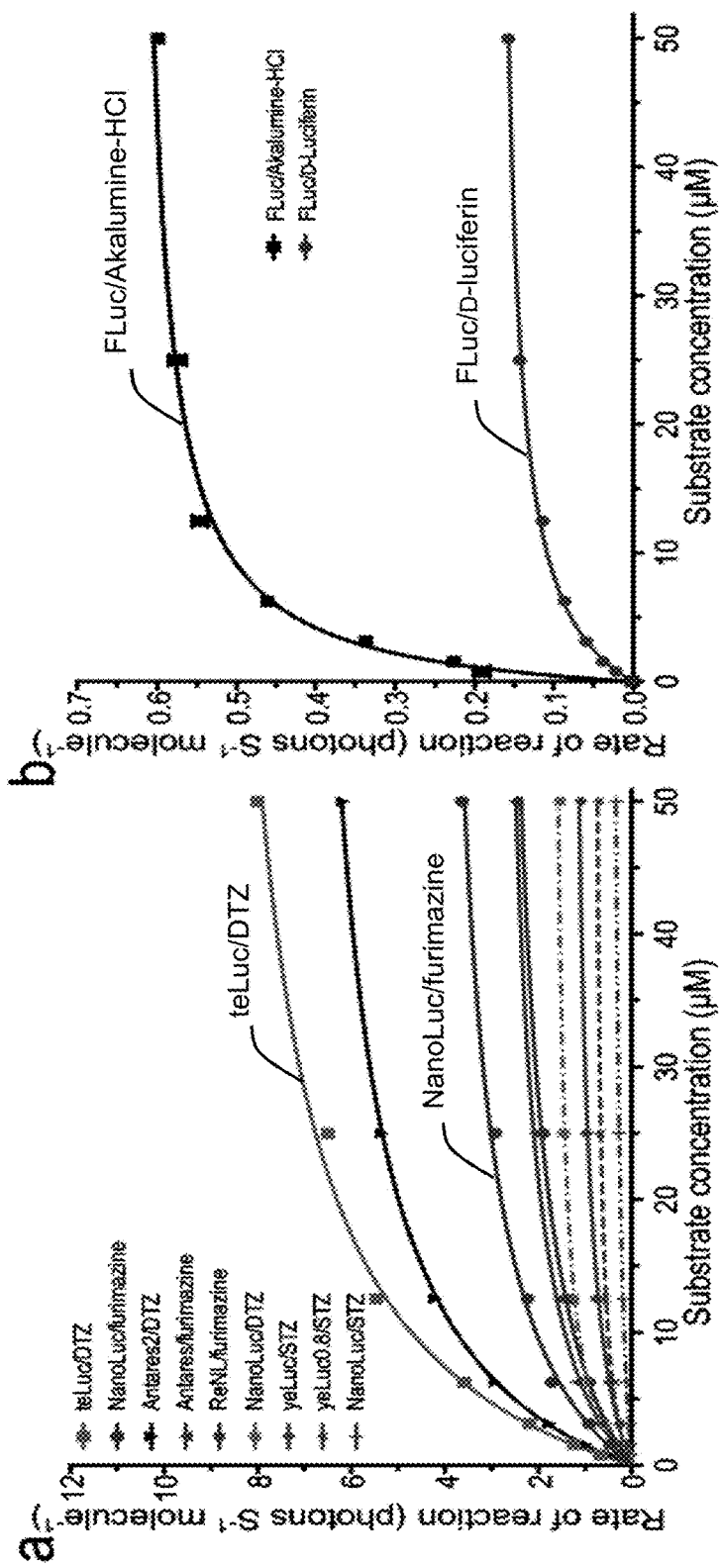
FIG. 8 is a panel of graphs showing substrate titrations with pure enzymes to determine apparent Michaelis constants ($K_m$). Titrations using new luciferases (8a) and Fluc (8b) are shown. The final concentrations of all enzymes were 100 pM. Substrate concentrations varied from 0.78 to 50 µM, and peak bioluminescence intensities at individual substrate concentrations were used to fit the Michaelis-Menten equation. Data are shown as mean and s.d. of three independent experiments.

Next, NanoLuc was engineered for enhanced activity toward either DTZ or STZ by simultaneously randomizing residues I44, I54, and I138 (FIG. 4), since these positions have been reported to modulate the substrate preference of NanoLuc (15). However, screening this library did not yield any useful mutants. Another library was subsequently screened with full randomization at residues L18, D19, R162, and C164 based on their proximity to a putative substrate-binding site (FIG. 5 and FIG. 6) (16). Random mutations were also introduced across the gene using error-prone PCR. From this, a NanoLuc mutant (NanoLuc-D19S/D85N/C164H) was identified with a 5.7-fold enhancement of DTZ bioluminescence, which was designated "teLuc" for its teal emission peak at 502 nm (Table 1, FIG. 1b, and FIG. 5). Additionally, another NanoLuc mutant (yeLuc0.8 or NanoLuc-L18Q/D19A/S28T/C164S) was identified displaying enhanced activity toward STZ. Further evolving yeLuc0.8 with three additional rounds of error-prone PCR and bacterial colony-based screening resulted in a variant with six additional mutations (yeLuc or yeLuc0.8-F1L/A14D/V27L/Q69R/R112Q/L142R). This new mutant shows an 11.5-fold overall enhancement of STZ bioluminescence over NanoLuc (Table 1, FIG. 1b, and Supplementary Table 1). teLuc/DTZ displayed sustained bioluminescence with an ~40 min half-life, whereas the fast decay of yeLuc/STZ emission has an ~5 min half-life (FIG. 7). The apparent Michaelis constants ($K_m$) for teLuc/DTZ and yeLuc/STZ were similar to those of NanoLuc/furimazine (FIG. 8), while the quantum yield of teLuc/DTZ doubled from that of NanoLuc/furimazine (Supplementary Table 1). Compared to FLuc/D-luciferin, teLuc/DTZ emitted 13 times more photons at wavelengths longer than 600 nm (FIG. 1b and Table 1).

TABLE 1

Photoluminescence properties of various luciferase-luciferin pairs.

| | Reporter | | Relative intensity [a] | | | | | |
|---|---|---|---|---|---|---|---|---|
| | | | Protein [b] | | HEK 293T Cells [c] | | Mice | |
| | $\lambda_{max}$ | size | | Intact | Intact | | Subcutaneously | Hydrodynamic transfection [e] |
| | (nm) | (kDa) | Total  >600 nm | (Total) | (695/50 nm) | Lysate | injected cells [d]  0.3 µmol | 3.3 µmol |
| NanoLuc + furimazine | 456 | 19 | 43.5  0.7 | 277 | 5 | 167 | 7.2  ND [f] | ND [f] |
| teLuc + DTZ | 502 | 19 | 113  13 | 733 | 55 | 317 | 54  52 | 136 |

TABLE 1-continued

Photoluminescence properties of various luciferase-luciferin pairs.

| | | | | Relative intensity [a] | | | | | |
|---|---|---|---|---|---|---|---|---|---|
| | Reporter | | | HEK 293T Cells [c] | | | Mice | | |
| | $\lambda_{max}$ | size | Protein [b] | | Intact | Intact | | Subcutaneously | Hydrodynamic transfection [e] |
| | (nm) | (kDa) | Total | >600 nm | (Total) | (695/50 nm) | Lysate | injected cells [d] | 0.3 μmol | 3.3 μmol |
| yeLuc + STZ | 527 | 19 | 13 | 3.7 | 78 | 21 | 6.5 | 1.8 | 3.5 | ND [f] |
| FLuc + D-luciferin | 563 | 61 | 1 | 1 | 1 | 1 | 1 | 1 | 1 | 4.4 [g] |
| FLuc + AkaLumine-HCl | 677 | 61 | 3.4 | 8.7 | 2.3 | 10 | 11 | 1.3 | ND [f] | 9.3 |
| ReNL + furimazine | 459, 583 | 71.8 | 26 | 13 | 159 | 130 | 100 | ND [f] | ND [f] | ND [f] |
| Antares + furimazine | 456, 583 | 70.5 | 30 | 17 | 160 | 137 | 112 | 26 | 65 | 115 |
| Antares2 + DTZ | 501, 583 | 70.5 | 79 | 65 | 601 | 268 | 252 | 57 | 97 | 182 |

[a] Intensity values normalized to FLuc/D-luciferin under comparable experimental conditions;
[b] 30 μM substrates and 100 pM proteins. Values are based on intensities integrated over the first 10 min post-substrate injection;
[c] 50 μM substrates and 2000 cells with an average transaction efficiency of ~70%;
[d] Subcutaneous injection of two million HEK 293T cells and 100 μL of 100 μM of each substrate;
[e] Intraperitoneal injection of each substrate. All intensity values are normalized to FLuc and 0.3 μmol D-luciferin;
[f] Not determined.
[g] The relative intensity increased to 11.8 when 10 μmol D-luciferin was intraperitoneally injected.

SUPPLEMENTARY TABLE 1

Photoluminescence properties of luciferase/luciferin pairs as determined by protein assays.

| | $\lambda_{max}$ (nm) | $K_m$ (μM) [a] | $k_{cat}$ (s$^{-1}$) [a] | QY (%) [a] | Relative overall emission [b] |
|---|---|---|---|---|---|
| NanoLuc/CTZ | 458 | ND [c] | ND [c] | ND [c] | 3.3 [d] [3.2] [e] |
| NanoLuc/furimazine | 456 | 11.5 ± 0.6 | 88.2 ± 1.7 | 510.2 | 45.5 [d] [43.5] [e] |
| NanoLuc/DTZ | 500 | 5.3 ± 0.2 | ND [c] | ND [c] | 20 [d] [22.2] [e] |
| NanoLuc/STZ | 527 | 17.8 ± 1.0 | ND [c] | ND [c] | 1.5 [d] [1.57] [e] |
| teLuc/DTZ | 502 | 10.2 ± 0.4 | 88.1 ± 0.1 | 10.8 ± 0.5 | 114 [d] [113] [e] |
| yeLuc0.8/STZ | 527 | 6.3 ± 0.5 | ND [c] | ND [c] | 11.4 [d] [7.4] [e] |
| yeLuc/STZ | 527 | 11.9 ± 0.9 | 175 ± 5 | 0.8 ± 0.1 | 17.3 [d] [12.6] [e] |
| FLuc/D-luciferin | 563 | 6.3 ± 0.2 | 0.4 ± 0.005 | 44 ± 1.2 | 1 [d] [1] [e] |
| FLuc/AkaLumine-HCl | 677 | 2.4 ± 0.2 | ND [c] | ND [c] | 2.8 [d] [3.4] [e] |
| ReNL/furimazine | 459, 583 | 14.5 ± 1.3 | 104 ± 4 | 2.6 ± 0.2 | 28.4 [d] [25.7] [e] |
| Antares/furimazine | 456, 583 | 11.1 ± 0.5 | 112 ± 2 | 2.7 ± 0.3 | 32.7 [d] [29.6] [e] |
| Antares2/DTZ | 501, 583 | 9.7 ± 0.2 | 86.1 ± 0.7 | 8.6 ± 0.3 | 82.5 [d] [79.4] [e] |

[a] mean ± s.d., n = 3 (see Online Methods for details);
[b] Intensity values normalized to FLuc/D-luciferin under comparable conditions with purified recombinant proteins (30 μM substrates and 100 pM proteins), respectively;
[c] Not determined;
[d] Maximal intensity;
[e] Integrated intensity over the first 10 min.

Figure 9:
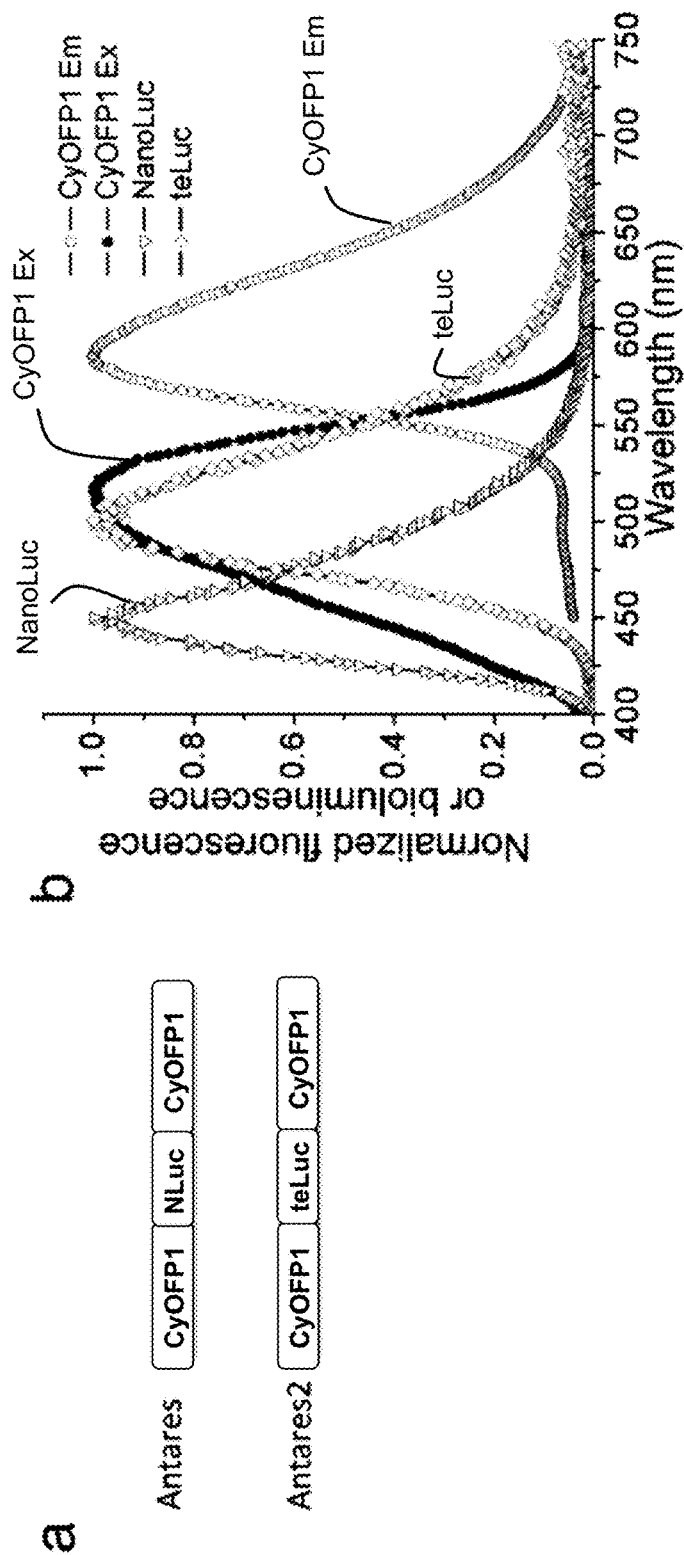
FIG. 9 is a panel showing domain arrangement and spectral overlap of Antares2. (9a) Primary structural arrangement of Antares and Antares2. (9b) Fluorescence and bioluminescence profiles of CyOFP1, NanoLuc, and teLuc, showing a better BRET spectral overlap between teLuc and CyOFP1 than between NanoLuc and CyOFP1. The BRET efficiency increased from 67% in Antares to 71% Antares2 by comparing the intensities of Antares, Antares2, NanoLuc, and teLuc at the same concentrations (also see FIG. 1b).

Recently, NanoLuc was fused to fluorescent proteins for BRET-based reporters, including the two most red-shifted variants, Antares and ReNL (17,18). In particular, the absorbance of CyOFP1 in Antares overlaps better with teLuc/DTZ emission than with NanoLuc/furimazine (FIG. 9). Replacing NanoLuc with teLuc in Antares resulted in a BRET-based Antares2 reporter emitting 65 times more photons above 600 nm than FLuc/D-luciferin (FIG. 1b and Table 1).

Figure 10:
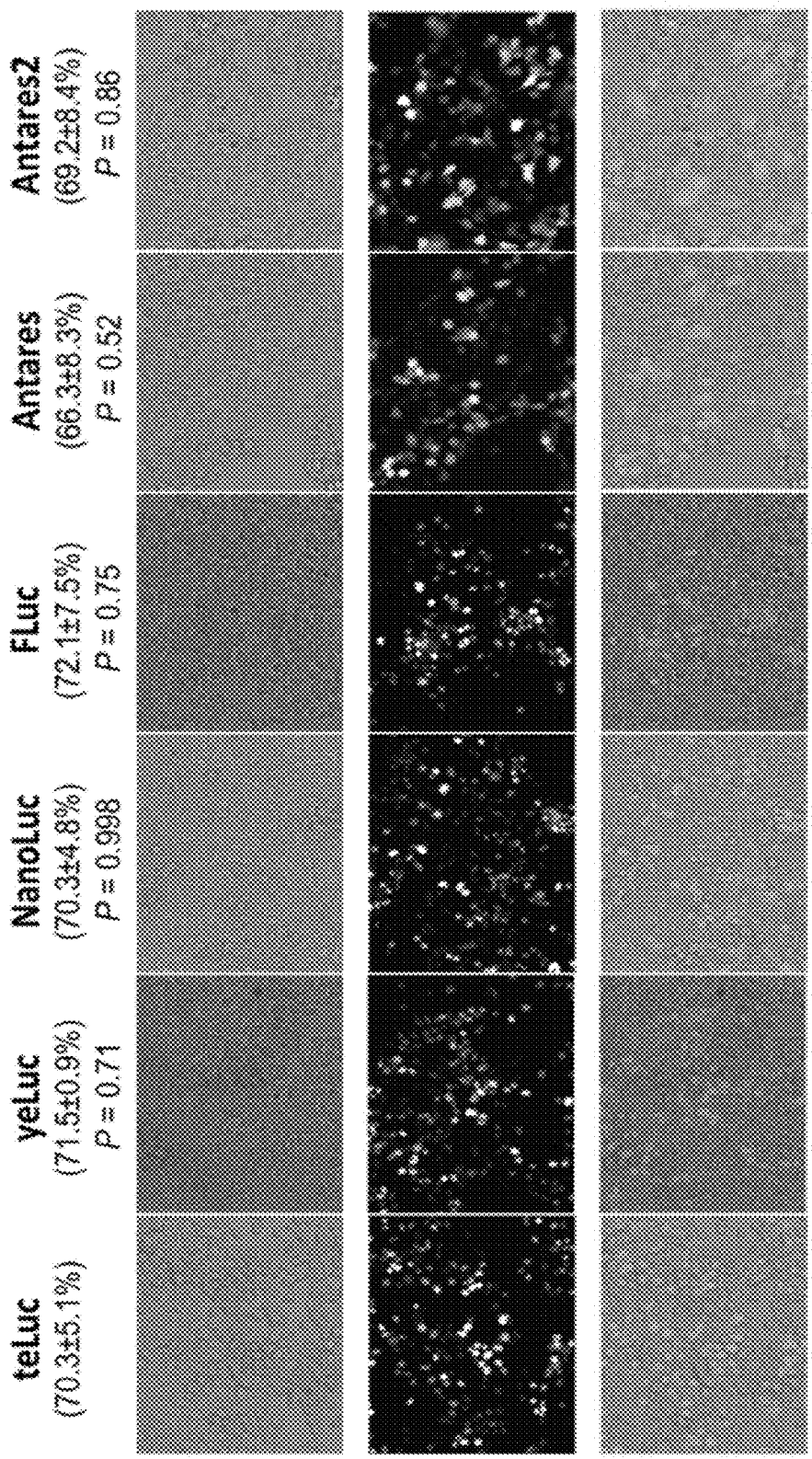
FIG. 10 is a panel showing evaluation of transfection efficiencies. Cells liposomally co-transfected with the indicated luciferase and a nuclear localized red fluorescent protein (pNuc-mCherry) were evaluated by fluorescence microscopy. Exceptions are Antares and Antares2, which were directly imaged for CyOFP1 fluorescence. Transfection efficiencies are indicated in parentheses (mean±s.d.) and were derived from three independent replicates. P values were based on unpaired two-tailed t-tests for individual luciferases in reference to teLuc. The results support that we can reproducibly and consistently transfect HEK 293T cells for comparison of luciferases.
Figure 11:
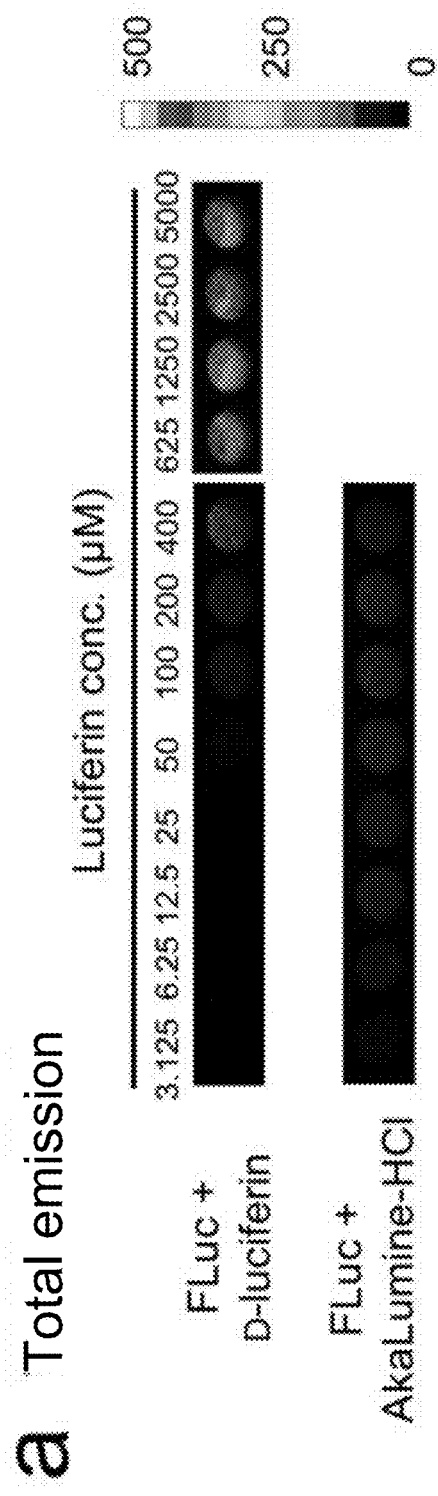
FIG. 11 is a panel of representative pseudocolored images and quantifications of luciferase-expressing HEK 293T cells. Images were acquired without a filter (11a) or with a 695±25 nm NIR emission filter (11c). Panels 11b and 11d are quantification results for Panels 11a and 11c, respectively. All values were normalized to the intensities of FLuc/D-luciferin (50 µM) under the same imaging conditions. Data are shown as mean and s.d. of three independent experiments. The bioluminescence intensity of FLuc with millimolar D-luciferin or AkaLumine-HCl was still 1-2 orders of magnitude lower than that of teLuc or Antares2 in the presence of micromolar DTZ (also see FIG. 1c-f).
Figure 11:
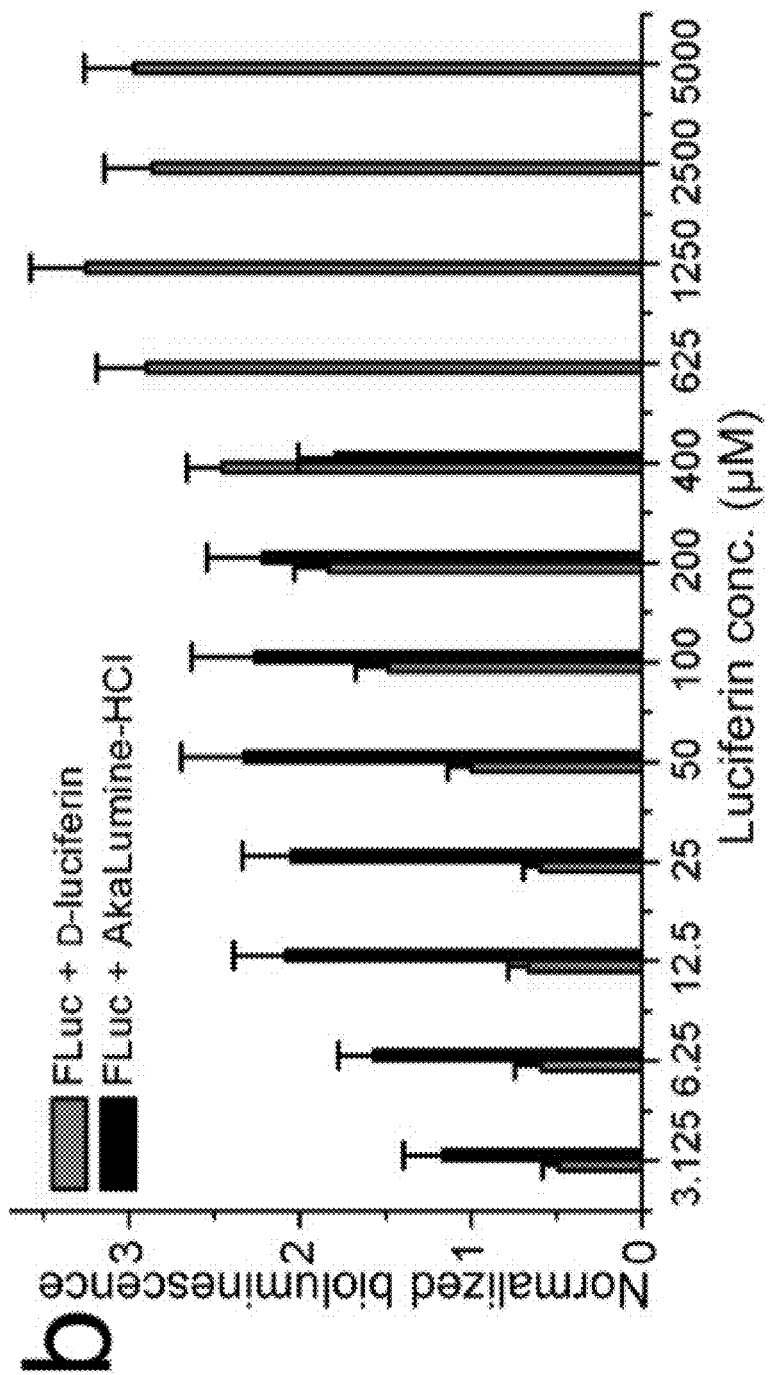
Figure 11:
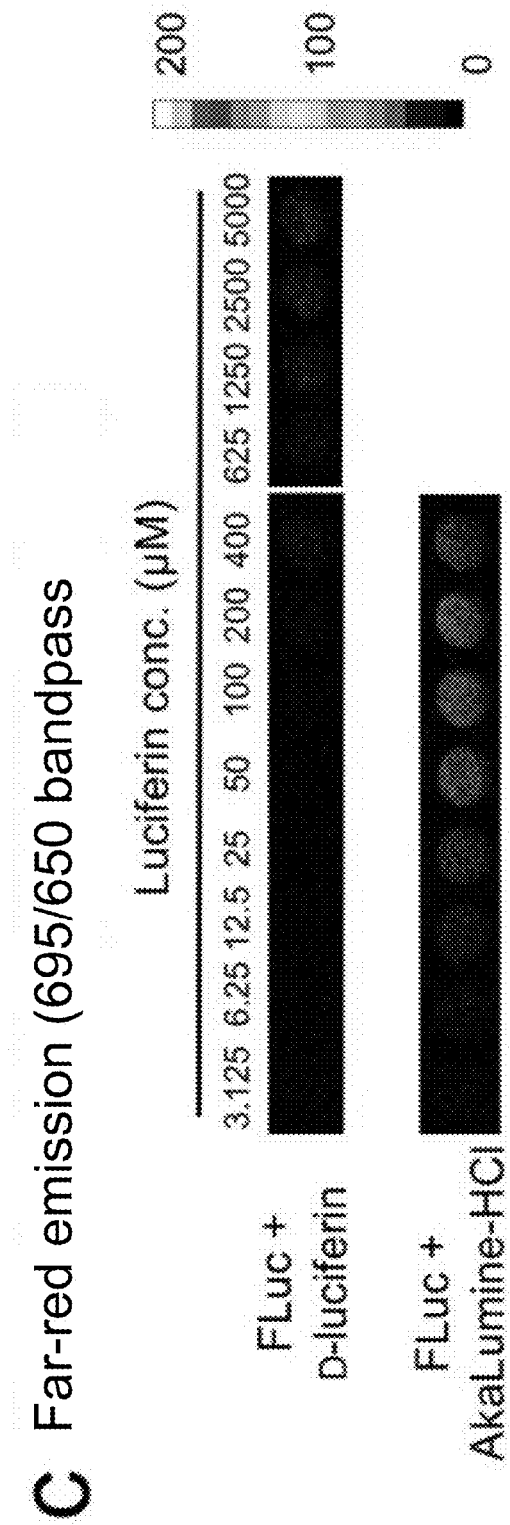
Figure 11:
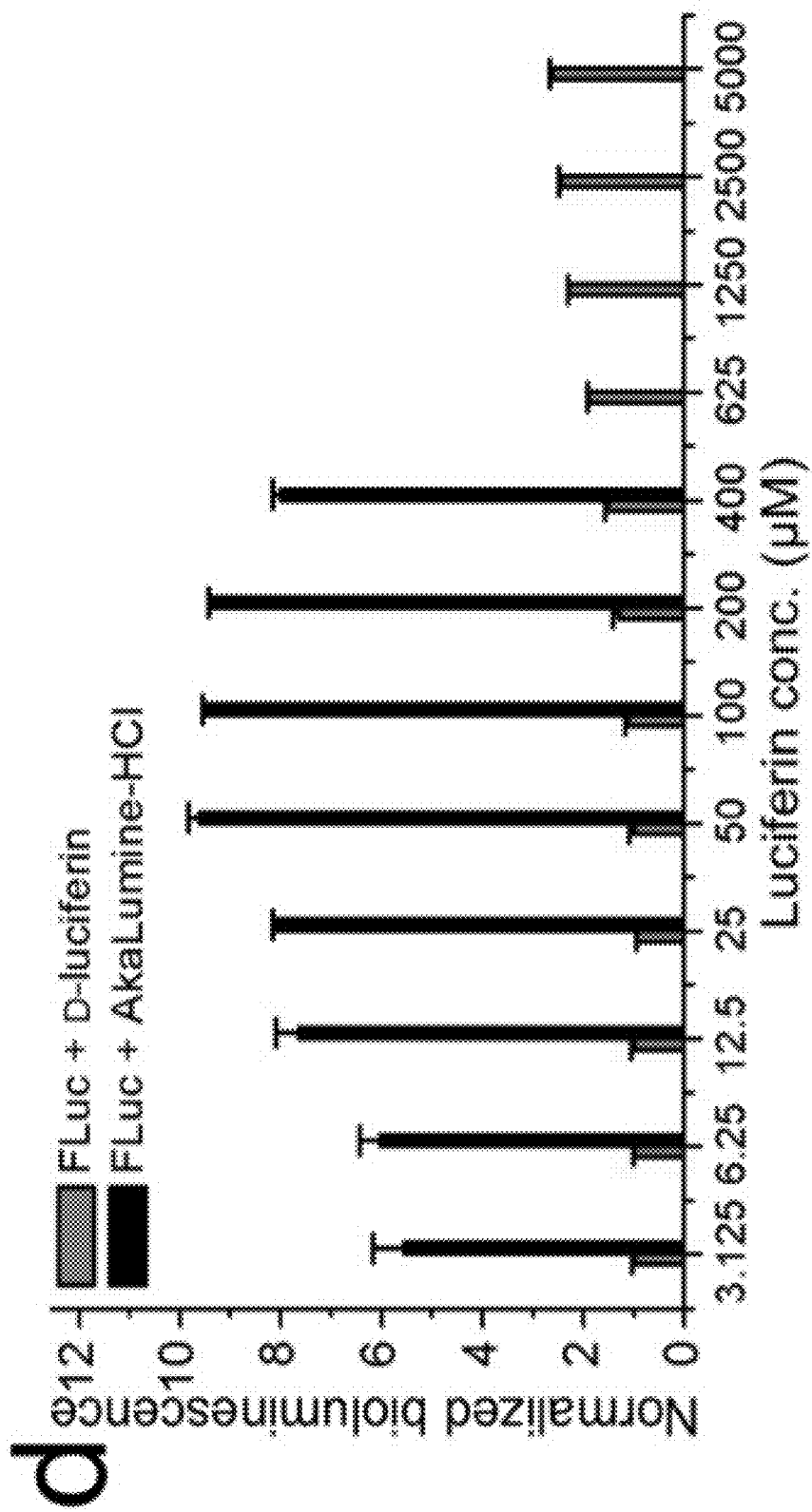
Figure 12:
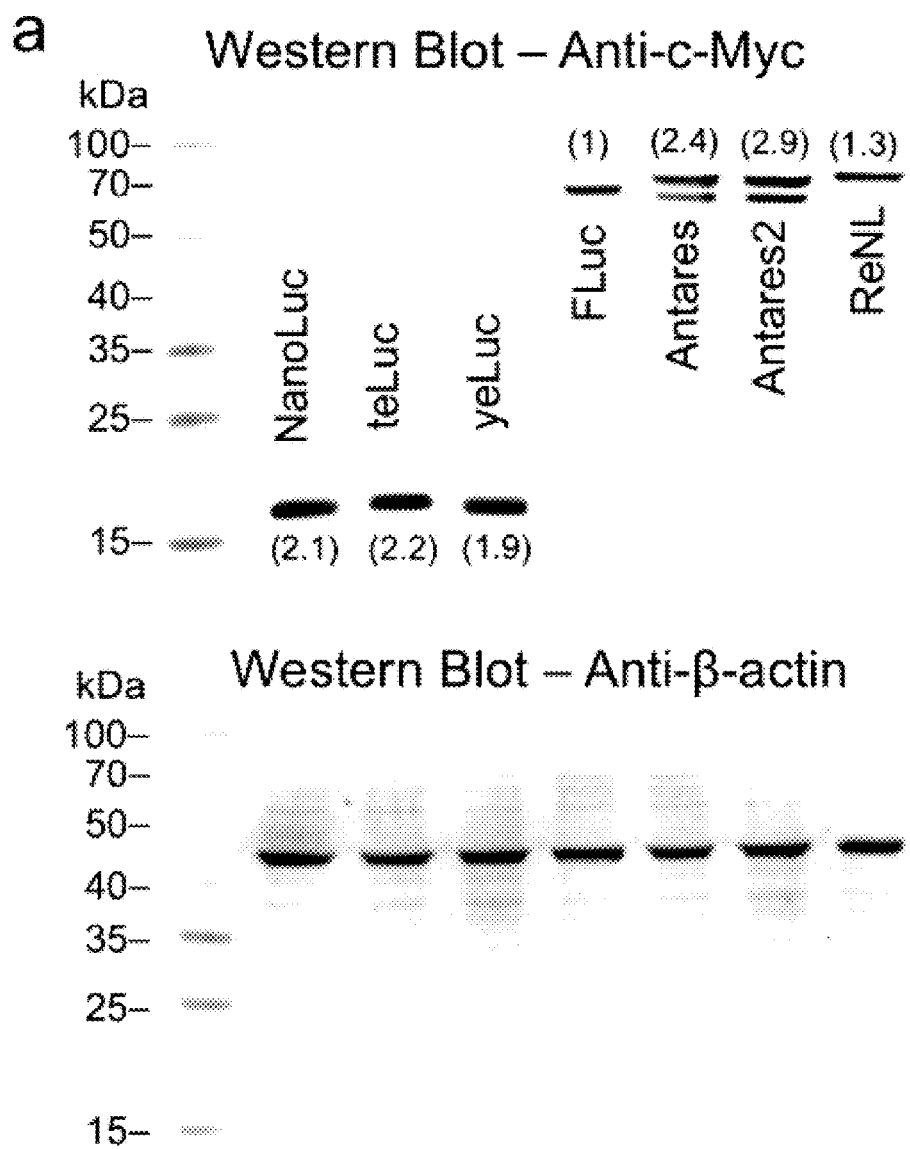
FIG. 12 is a panel examining the impact of luciferase protein levels on bioluminescence intensities. (12a) Western blot analysis of HEK 293T cells expressing luciferases with C-terminal c-Myc tags. The relative proteins levels quantified from individual bands are shown in parentheses. These enzymes were expressed at different levels but the differences were within 3-fold. (12b) Bioluminescence of NanoLuc and teLuc relative to FLuc when expressed using P2A bicistronic vectors. Under this condition, two luciferases in the same vectors are expected to be expressed near-stoichiometrically. 10,000 HEK 293T cells transfected with Construct 1 or Construct 2 were equally split and mixed with 30 µM of DTZ, furimazine, or D-luciferin. The signals were integrated for the first 2 min and the ratios of total NanoLuc or teLuc emission to total FLuc emission were calculated. Large bioluminescence enhancements by NanoLuc and teLuc were observed. Data are shown as mean and s.d. of three independent experiments.
Figure 12:
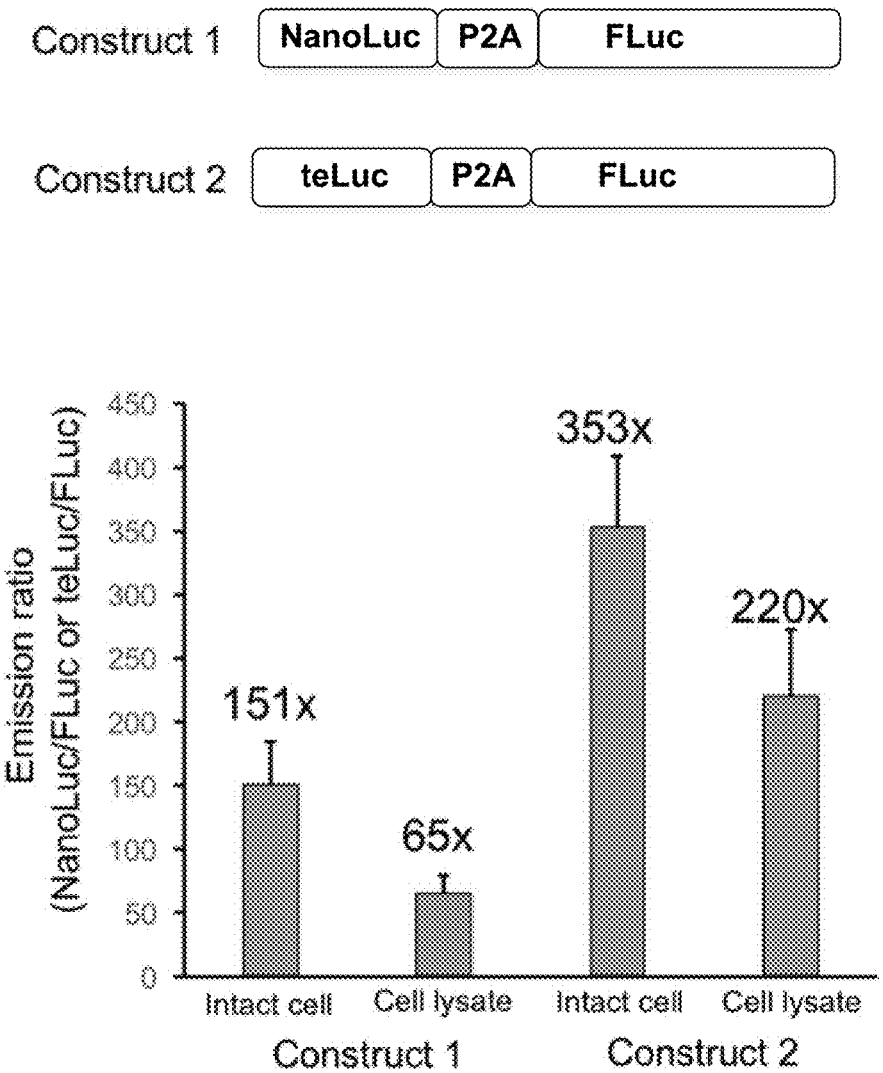
Figure 13:
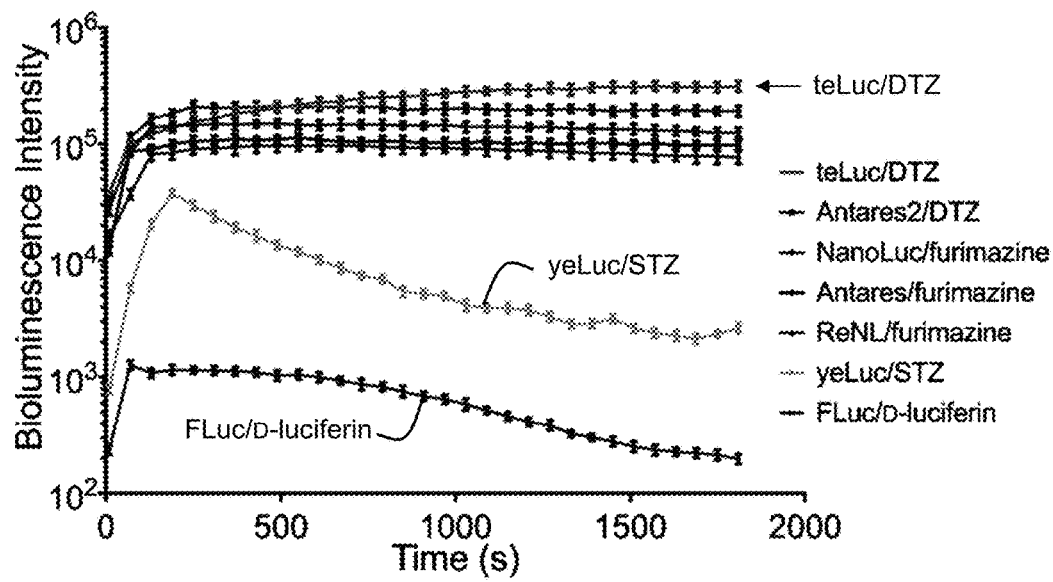
FIG. 13 is a graph showing bioluminescence decay kinetics in intact HEK 293T cells. The assay was performed with 30 µM substrates in a 96-well plate format containing corresponding 5000 luciferase-expressing HEK 293T cells in DPBS. Bioluminescence intensities were measured at 60 s intervals after substrate addition. Data are shown as mean and s.d. of three independent experiments.
Figure 14:
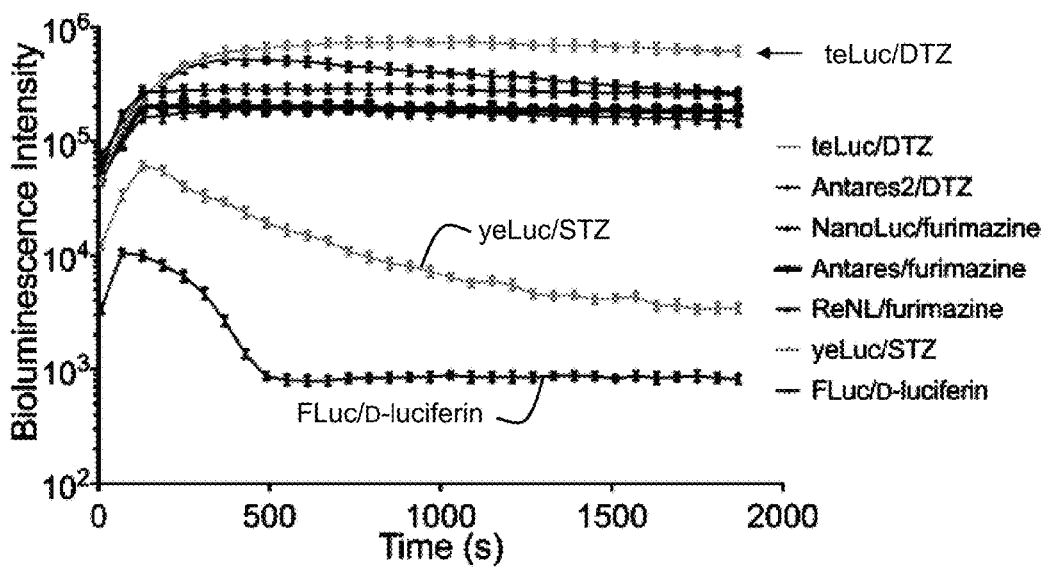
FIG. 14 is a graph showing bioluminescence decay kinetics in HEK 293T cell lysates. Corresponding substrates (30 µM) were added into cell lysates of ~5000 cells in a 96-well plate format. Bioluminescence intensities were measured at 60 s intervals after substrate addition. Data are shown as mean and s.d. of three independent experiments.
Figure 15:
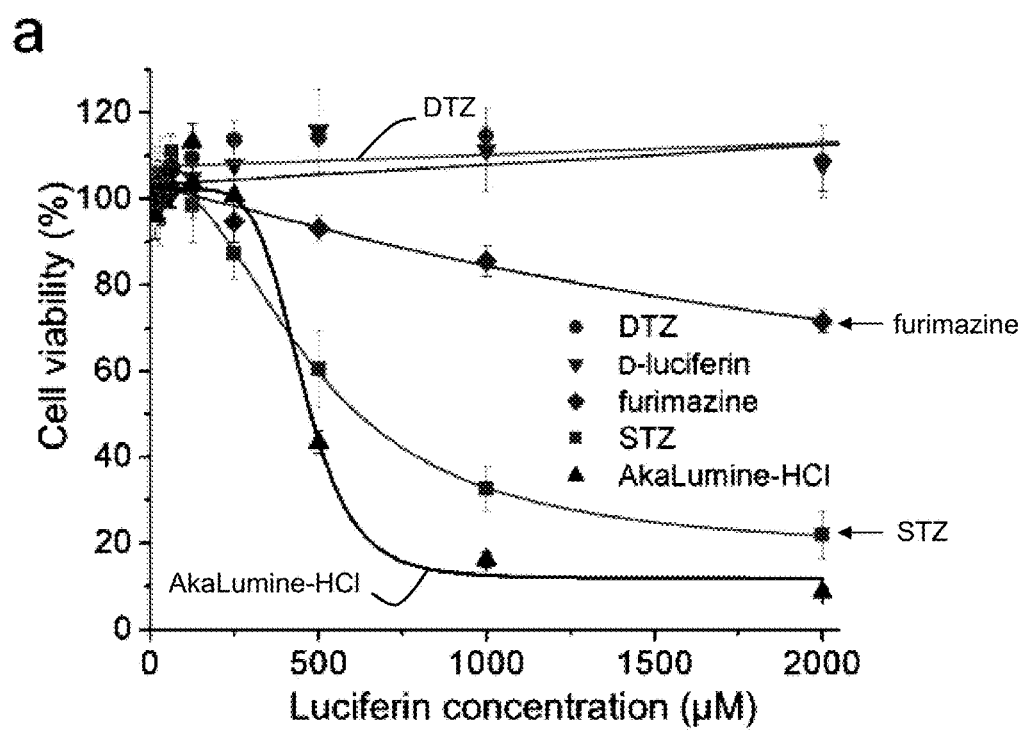
FIG. 15 is a panel showing the evaluation of the cytotoxicity of various luciferins. (15a) Viability of HEK 293T cells determined using RealTime-Glo™ MT Cell Viability Assay (Promega) after incubation with individual luciferin substrates for 24 h at 37° C. (15b) Evaluation of cell morphology and staining of dead cells. Cells incubated with the indicated luciferins for 24 h at 37° C. were stained with propidium iodide (PI), a fluorescent dye for dead cells. The cytotoxicity of STZ, furimazine, and AkaLumine was further confirmed by the red fluorescence of PI. Data are shown as mean and s.d. of three independent experiments.
Figure 15:
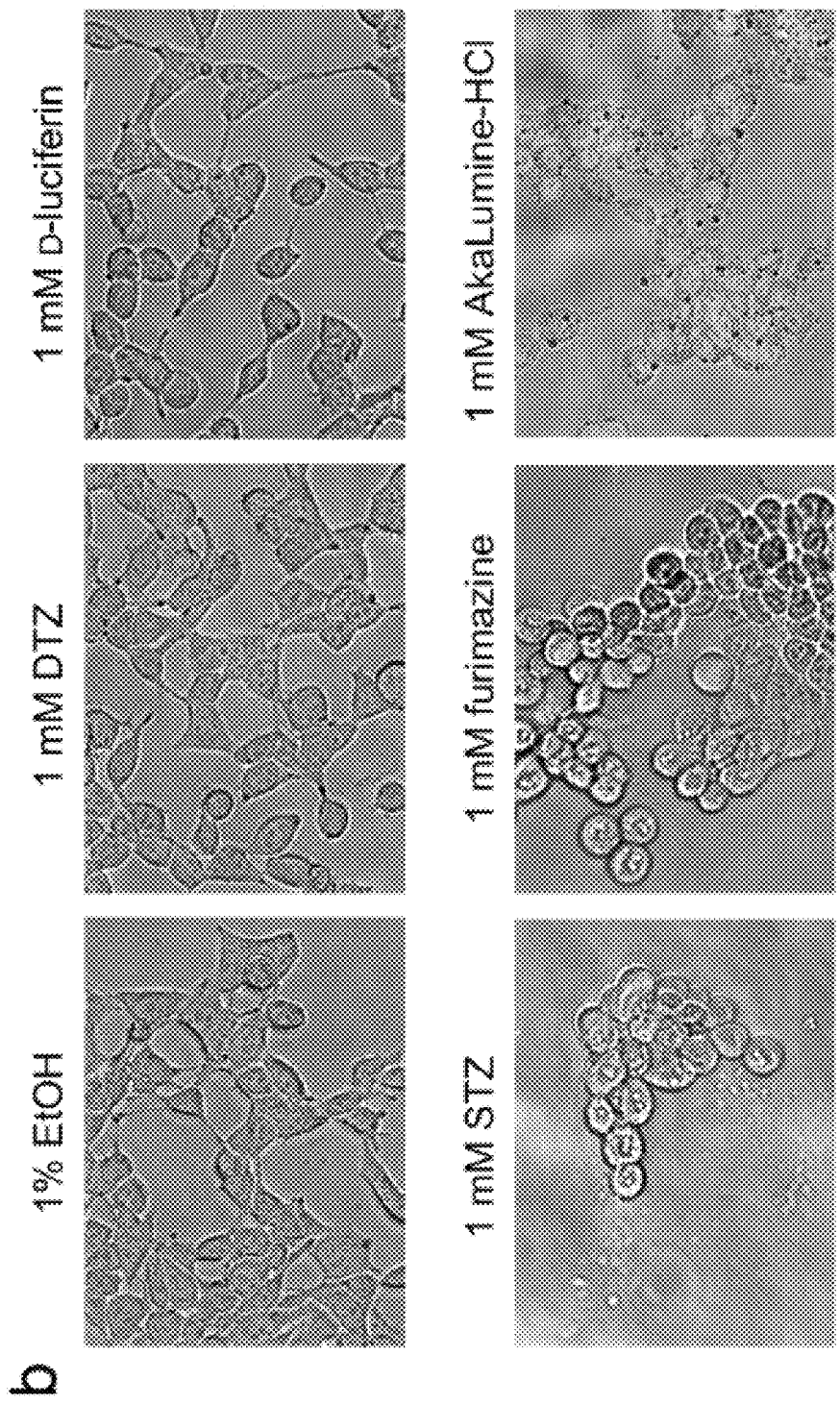

The bioluminescence of the new reporters was further evaluated using transiently transfected Human Embryonic Kidney (HEK) 293T cells (FIG. 10). Under all conditions, the brightness of DTZ with teLuc or Antares2 was two to three orders of magnitude higher than that of FLuc/D-luciferin (FIG. 1c-f, Table 1, and FIG. 11). These enhancements were more dramatic than the results observed in protein assays because of the high levels of teLuc and Antares2 in live cells (FIG. 12) and better cell permeability of our synthetic substrates. teLuc and Antares2 also displayed improvements over NanoLuc, Antares, and ReNL (Table 1). teLuc emitted sustained bioluminescence with a half-life of >2 h in both intact cells and cell lysates, whereas yeLuc showed flash-type kinetics (FIGS. 13,14). Moreover, DTZ elicits minimal cell toxicity at millimolar concentrations (FIG. 15). In contrast, AkaLumine-HCl, furimazine, and STZ induced cell death within the tested substrate concentration range.

Figure 2:
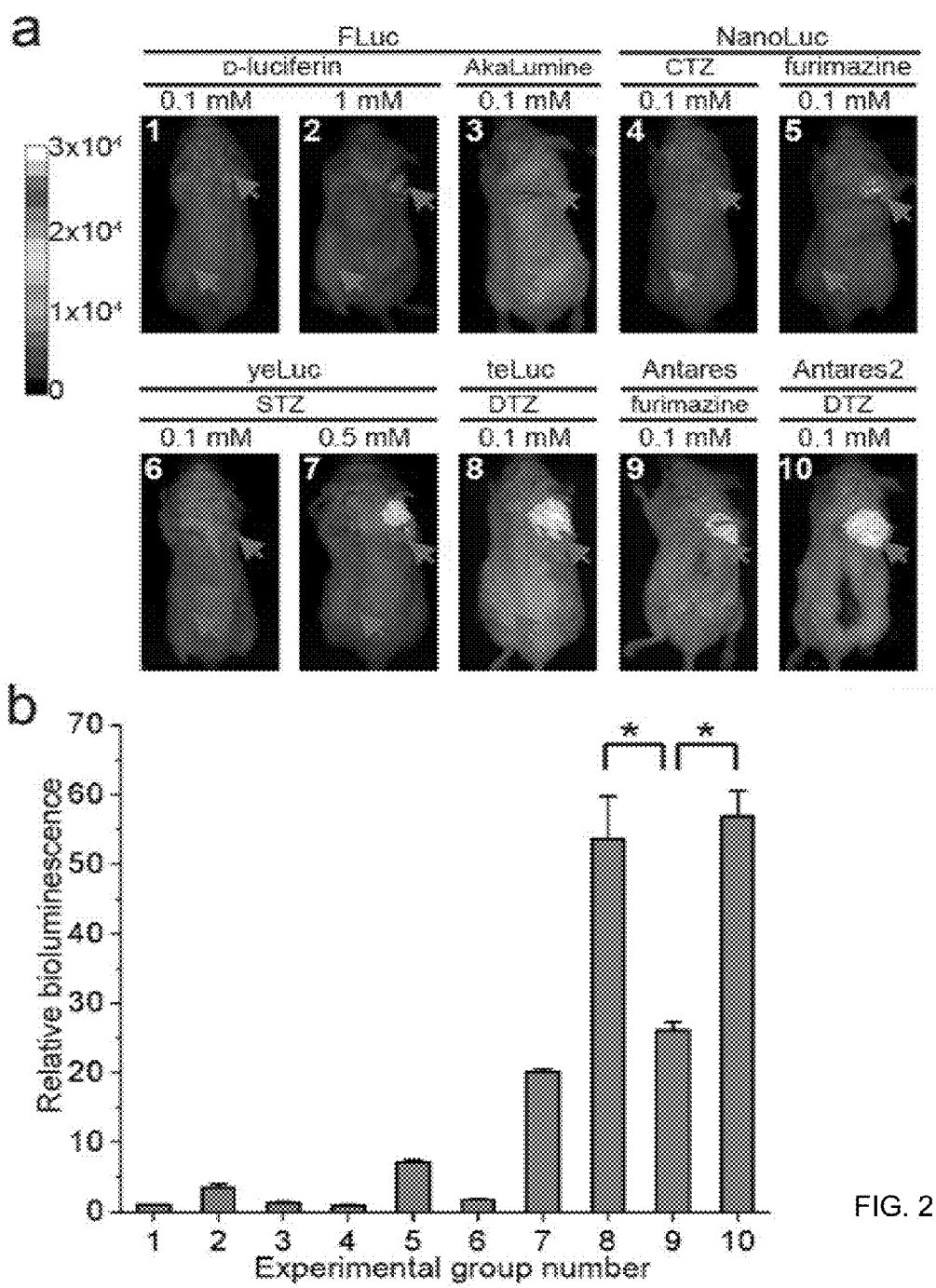
FIG. 2 is a panel showing bioluminescence imaging of luciferase-luciferin pairs at superficial sites and in deep tissues of live mice. (2a,2b) Representative bioluminescence images (2a) and quantitative analysis (2b) of BALB/c mice with subcutaneously injected luciferase-expressing HEK 293T cells and 100 µL luciferin substrates at the indicated concentrations. The group numbers in panel 2b are aligned with those in panel 2a. Two injection sites (one for luciferase-expressing cells and one for empty vehicle controls) for each mouse are illustrated with red arrows. Intensity values were normalized to the intensity of FLuc/D-luciferin (0.1 mM) acquired under the same condition. Data are shown as mean and s.d. (n=3). (2c,2d) Representative bioluminescence images (2c) and quantitative analysis (2d) of BALB/c mice, to which luciferase-coding plasmids were hydrodynamically delivered through tail vein injection, and luciferase substrates were intraperitoneally injected at 12 h post-plasmid injection. Intensity values were normalized to the intensity of FLuc/D-luciferin (0.3 µmol). Data are shown as mean and s.d. (n=4 for teLuc, Antares, and Antares2 with 3.3 µmol substrates, and n=3 for all other groups). Unpaired two-tailed t-tests were used to compare values between teLuc/DTZ and Antares2/DTZ with Antares/furimazine and FLuc/D-luciferin (*P<0.05), indicating the existence of a significant enhancement by teLuc and Antares2.
Figure 2:
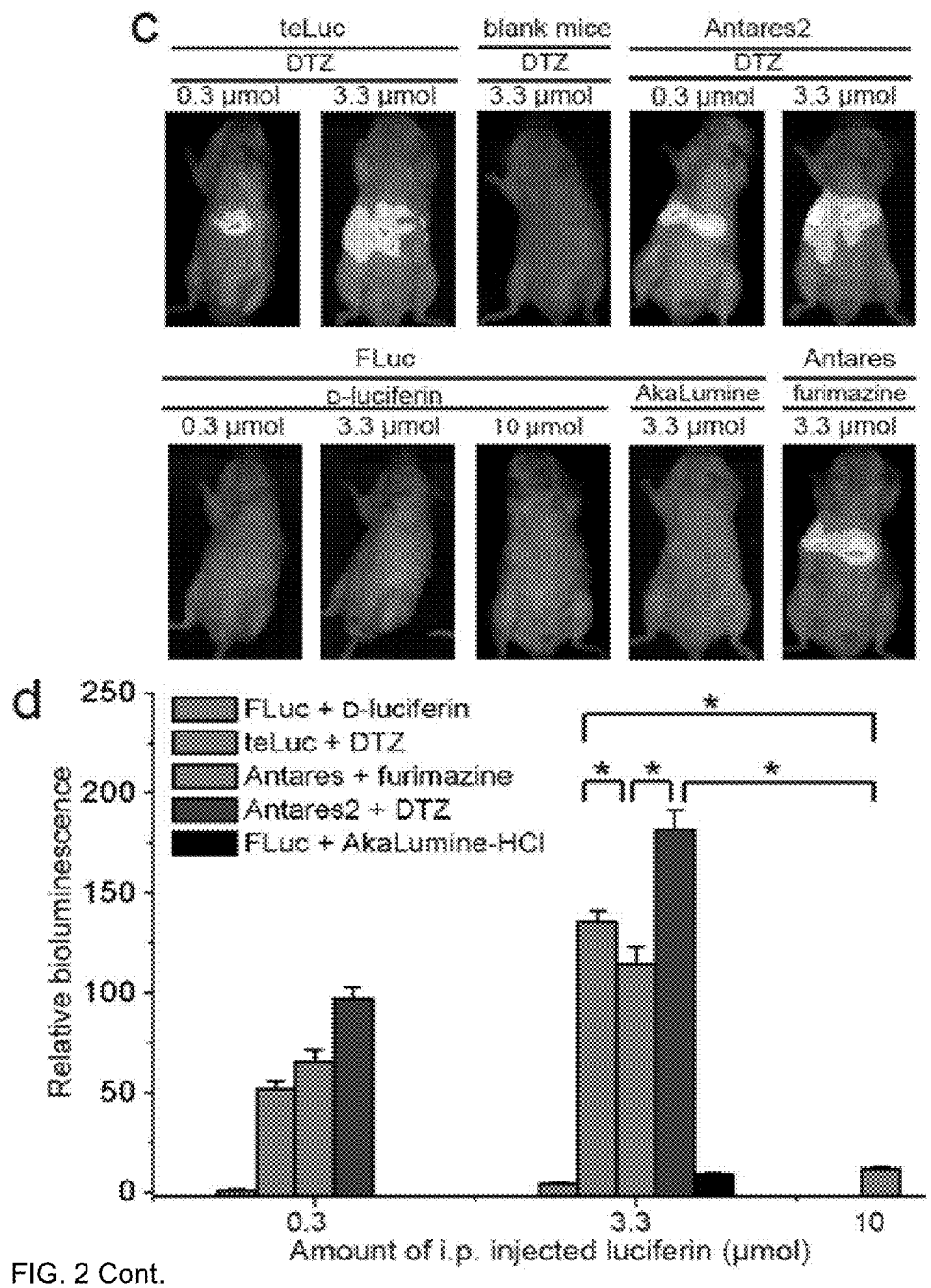
Figure 16:
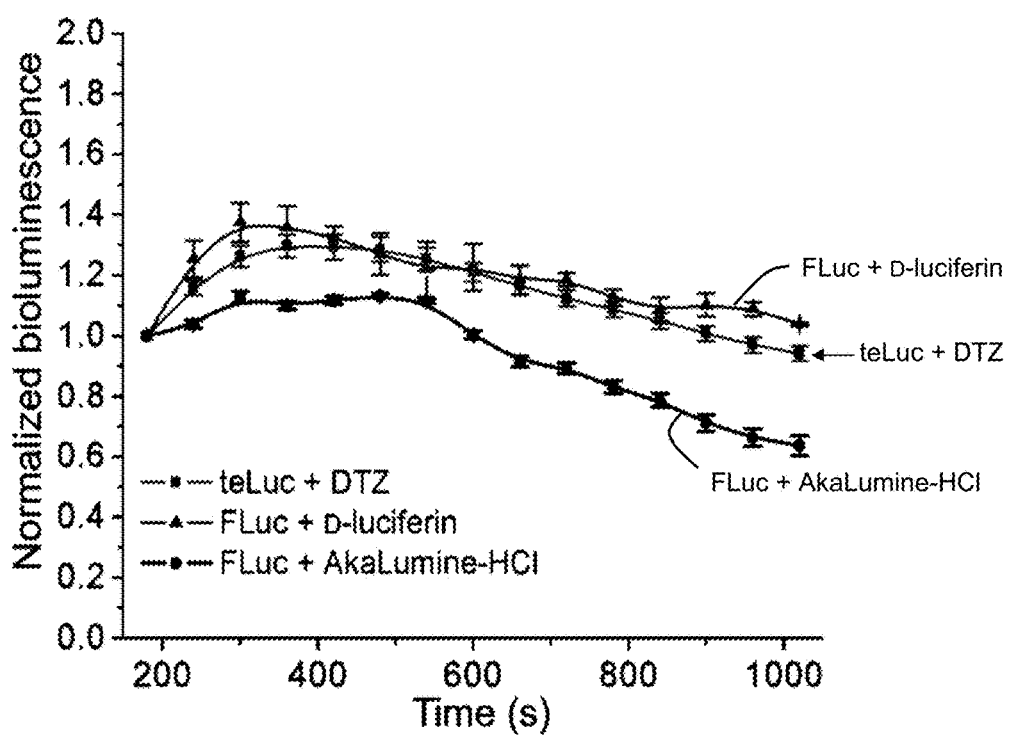
FIG. 16 is a graph of bioluminescence kinetics of IP injected luciferins (3.3 µmol each) in hydrodynamically transfected mice. Values are normalized to the starting intensities (t=180 s post-injection) and shown as mean and s.d. of three independent experiments.
Figure 17:
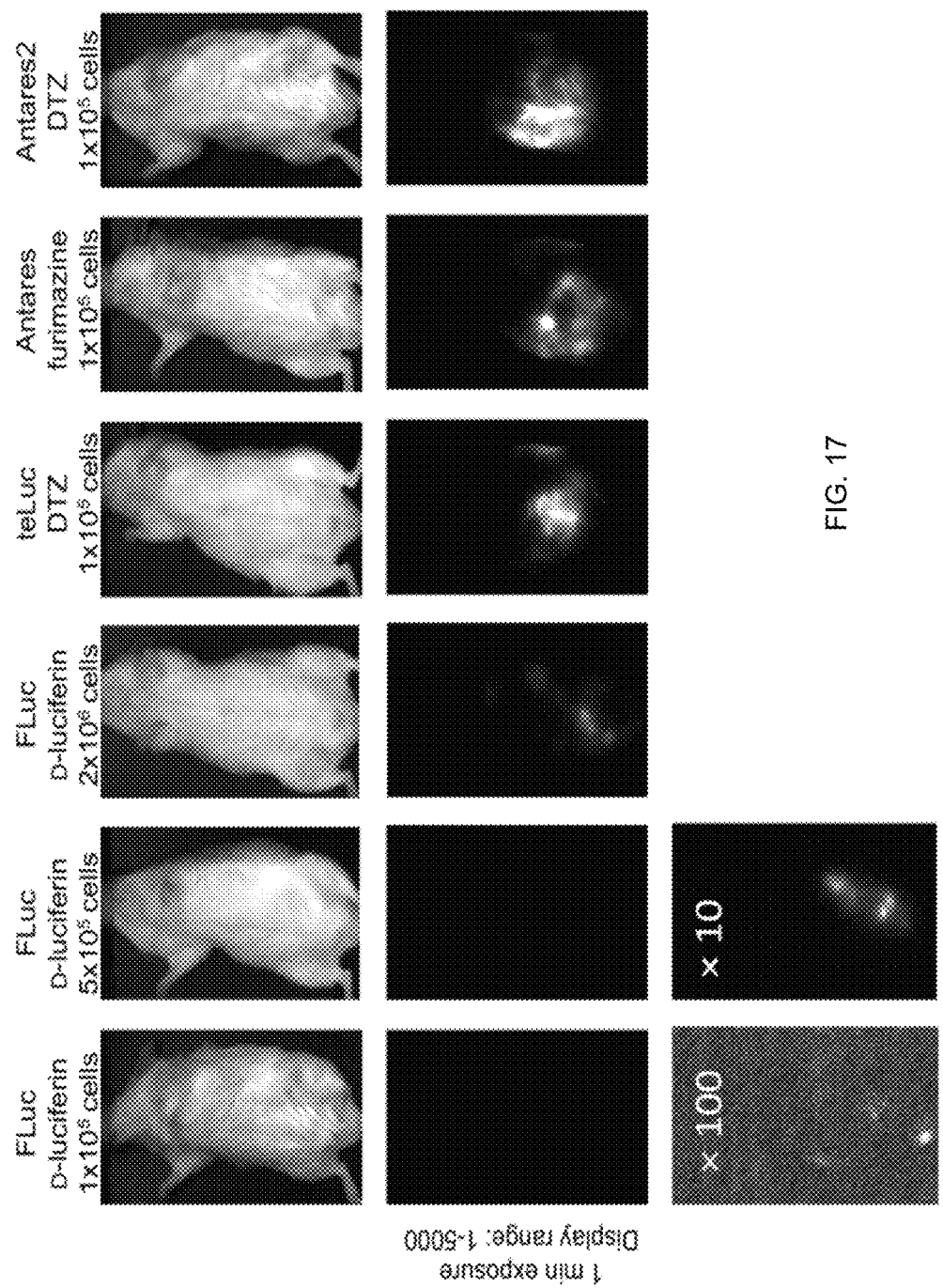
FIG. 17 is a panel of representative images of BALB/c mice with intravenously injected luciferase-expressing HEK 293T cells and intraperitoneally injected luciferin substrates. 3.3 µmol D-luciferin, 0.3 µmol DTZ, and 0.3 µmol furimazine were used in these experiments. Since the bioluminescence of FLuc/D-luciferin was very low after injecting 1×10⁵ or 5×10⁵ cells, the corresponding bioluminescence images are also shown in the bottom row after a 100- or 10-fold upscaling. The minimal threshold for the detection by FLuc/D-luciferin was 5×10⁵ cells. In contrast, the signals from 1×10⁵ cells expressing teLuc, Antares, or Antares2 were well above the background. These experiments were repeated three times.

The use of the new reporters was explored for in vivo BLI. To compare bioluminescence at superficial sites, HEK 293T cells expressing individual luciferases were subcutaneously injected near the right, dorsolateral trapezius region of unshaved BALB/c mice. For comparison, subcutaneously administered cells transfected with an empty vehicle to the same mice at the left, dorsolateral thoracolumbar region were also injected. These injections were followed up with an additional subcutaneous luciferin injection. At a 0.1 mM substrate concentration, teLuc/DTZ was ~54-fold brighter than FLuc/D-luciferin, and ~7.5-fold brighter than NanoLuc/furimazine (FIG. 2a,2b and Table 1). The brightness of Antares2 was comparable to that of teLuc, and no background bioluminescence was observed from sites injected with vehicle-transfected cells. To further evaluate the reporters for imaging deep-tissue targets, hydrodynamic transfection was utilized to express luciferase genes within the internal organs of mice. After intraperitoneal injections of 0.3 μmol individual luciferin substrates, teLuc/DTZ generated ~52-fold higher emission than FLuc/D-luciferin (FIG. 2c,2d and Table 1). With 3.3 μmol of each substrate (a dose recommended for AkaLumine-HCl [9]), teLuc/DTZ was ~31-fold brighter than FLuc/D-luciferin and ~15-fold brighter than FLuc/AkaLumine-HCl. Moreover, teLuc with 3.3 μmol DTZ was still ~12-fold brighter than FLuc with 10 μmol D-luciferin (equivalent to the standard ~150 mg/kg FLuc imaging condition). DTZ injections into untransfected BALB/c mice did not yield any background emission (FIG. 2c). When used for deep-tissue imaging, Antares2 shows an additional 30-80% signal increase over teLuc. Furthermore, the bioluminescence resulting from intraperitoneally injected DTZ displayed extended kinetics (FIG. 16), suggesting that both teLuc and Antares2 are suitable for time-lapse BLI. To further demonstrate the use of these new bioluminescent reporters to detect low-abundant targets, luciferase-expressing cells were intravenously injected into unshaved BALB/c mice. Despite that $5\times10^5$ FLuc-expressing cells were only marginally detectable, $1\times10^5$ teLuc or Antares2 labeled cells generated signals well above the background (FIG. 17).

In summary, CTZ analogues have been synthesized with modifications at the C-8 position and re-engineered Nano-Luc luciferase to catalyze these new substrates, thereby leading to brighter and more red-shifted bioluminescence. Despite that the water solubility of these CTZ analogs is worse than that of D-luciferin, the corresponding bioluminescence reactions with low amounts of the CTZ analogs are much brighter than FLuc with D-luciferin at saturated concentrations. In particular, teLuc/DTZ is one of the brightest bioluminescent systems showing robust performance in vitro, in cellulo, and in live mice. This will streamline a variety of applications to afford high sensitivity and reproducibility, and expanded the scope of BLI by allowing the use of less demanding instrumentation to track less abundant targets with higher spatiotemporal resolution. This study suggests that CTZ modification at C-8 may be a viable way to red-shift the bioluminescence of CTZ-utilizing enzymes. Moreover, it demonstrates the general feasibility of co-engineering CTZ-utilizing luciferases and substrates for improved bioluminescence. Increased detection sensitivity is not the only advantage of teLuc/DTZ. The small sizes of NanoLuc and its derived teLuc and yeLuc (19 kDa), compared to FLuc (61 kDa) and some other luciferases, facilitate their use as reporters to track protein dynamics, and to assemble viral vectors with limited packaging capacities. Moreover, NanoLuc forms a β-barrel structure that is amenable to various genetic and structural manipulations, such as split and fragment complementation [19]. Furthermore, their bioluminescence is independent of $Mg^+$, $Ca^{2+}$, and ATP [5]. All these suggest that teLuc may be an excellent scaffold for the development of bioluminescent biosensors compatible to other popular optogenetic tools [20]. teLuc was fused with CyOFP1 to derive Antares2, which further improved bioluminescence detection in deep tissues. Antares2 is an optimal bioluminescent reporter when the molecular size of the reporter is not important and when CyOFP1 does not caused spectral crosstalk. Overall, this work provides several robust bioluminescent reporters, including teLuc and Antares2, which are expected to have broad applications.

Example 2

The Designing and Synthesis of CTZ Analogs

Several CTZ analogs have previously been prepared for red-shifted bioluminescence [1], although they typically give low emission with their tested luciferases [2-4]. Most of these analogs have not been directly tested with NanoLuc, and their impact on the bioluminescence of NanoLuc is still unknown because the spectral shift observed for one CTZ-utilizing luciferase is not necessarily transferable to another [1]. For example, although the extended conjugation at the C-6 position of 6-pi-OH-CTZ (FIG. 3) was shown to red-shift the bioluminescence of an RLuc mutant, Rluc8, by 47 nm, there was hardly any bioluminescence observed when using NanoLuc [5]. It was therefore reasoned that NanoLuc might have limited tolerance to structural changes at the C-6 position, and subsequently, efforts were focused on the derivatization of CTZ at the C-8 position. Introducing heteroatoms, such as selenium, into fluorescent dyes or D-luciferin is a proven strategy to red-shift fluorescence or bioluminescence emission [6-8]. Oxygen and sulfur atoms have also been introduced to the C-8 position of CTZ to shift the bioluminescence of RLuc to longer wavelengths [3,4]. On the basis of these results, it was hypothesized that introducing selenium to the C-8 position of CTZ could be effective to red-shift the bioluminescence of NanoLuc. Therefore selenoterazine (STZ) was designed and a synthetic route for this molecule was developed from inexpensive, commercially available chemicals in six steps with 5.2% overall yield (Supplementary Scheme 1). Also serendipitously prepared was another CTZ analog, diphenylterazine (DTZ), which extends the conjugation at C-8 through an aromatic ring. The precursor of DTZ was initially derived as a side-product during the synthesis of STZ. Later on, DTZ was tested with NanoLuc and was found to be one of the most useful CTZ analogs to enhance and red-shift the bioluminescence of NanoLuc. A reported procedure [9] was revised and diphenylterazine was prepared in large quantities from commercially available chemicals in two steps with 23.1% overall yield (Supplementary Scheme 2).

1) Method to synthesize selenoterazine (STZ)

Supplementary Scheme 1

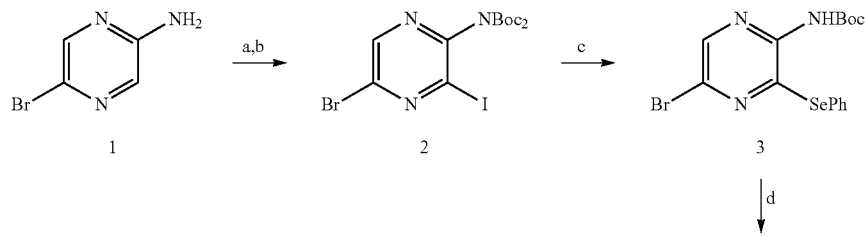

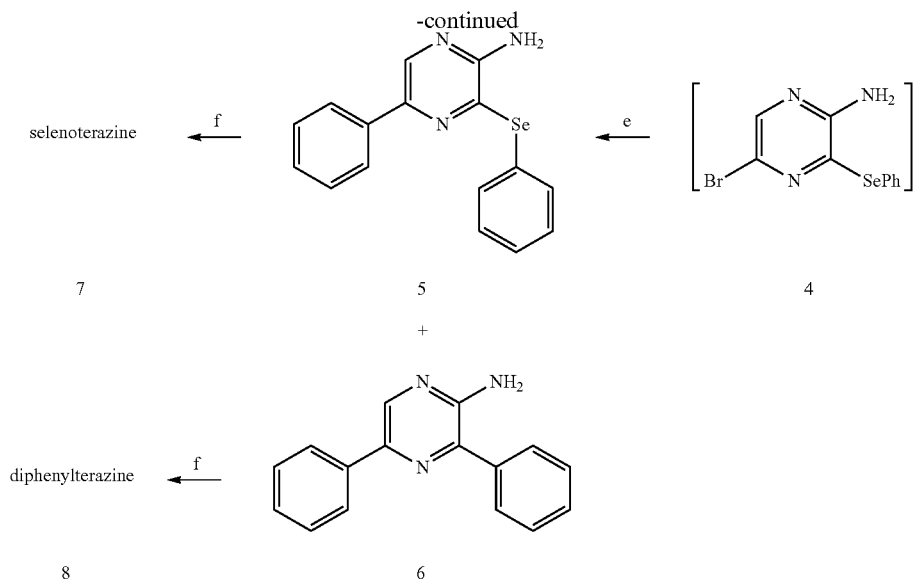

Scheme 1| Synthetic route for preparing selenoterazine (and diphenylterazine as a minor product): (a) TFA, NIS, ACN, Reflux; (b) (Boc)$_2$O, NEt$_3$, THF, RT, 85% from 1; (c) PhSe$_2$, Cu$_2$O, bpy, Mg, DMF, 85° C., 51%; (d) TFA, CH$_2$Cl$_2$, RT; (e) (C$_6$H$_5$CN)$_2$PdCl$_2$, (C$_6$H$_5$)$_2$P(CH$_2$)$_4$P(C$_6$H$_5$)$_2$, PhB(OH)$_2$, Na$_2$CO$_3$, toluene, EtOH, Reflux, 55% for 5 and 13% for 6 from 3; (f) PhCH$_2$COC(OEt)$_2$, 6N HCl, EtOH, Reflux, 22% for 7 and 35% for 8.

di-tert-butyl (5-bromo-3-iodopyrazin-2-yl)carbamate (2)

Trifluoroacetic acid (1.1 mL, 14.3 mmol) and N-iodosuccinimide (NIS, 7.76 g, 34.5 mmol) were added to a solution of 2-amino-5-bromopyrazine (1, 5 g, 28.7 mmol) in acetonitrile (50 mL) at 0° C. The mixture was stirred at reflux for 18 h under N2. After cooling to room temperature, the solvent was removed under reduced pressure. The residue was extracted with 50 mL ethyl acetate, neutralized and washed twice with saturated aq. NaHCO3 (50 mL), dried with anhydrous Na2SO4, filtered, and concentrated to give a black residue. The crude was next dissolved in dry THF (50 mL), to which was added Boc2O (13.78 g, 63.1 mmol) and triethylamine (12.1 mL, 86.2 mmol). The mixture was stirred under N2 for additional 5 h. The progress of the reaction was monitored with TLC (hexane/ethyl acetate=3:1). After completion of the transformation, MeOH (10 mL) was added to quench the reaction. The solvent was removed under reduced pressure. The residue was purified using column chromatography (silica gel; gradient elution with hexane/ethyl acetate from 20:1 to 5:1) to give compound 2 as white solid (9.7 g, 85% over two steps). 1H-NMR (CDCl3, 500 MHz): δ 8.46 (s, 1H), 1.41 (s, 18H); 13C-NMR (CDCl3, 125 MHz) δ 151.3, 149.0, 144.6, 136.8, 119.0, 84.7, 28.0; ESI-MS (C14H19BrIN3O4): [M+Na]+ calcd: 521.96, found: 521.95.

tert-butyl (5-bromo-3-(phenylselanyl)pyrazin-2-yl)carbamate (3)

Compound 2 (2.7 g, 5.4 mmol) and diphenyl diselenide (0.9 g, 2.9 mmol) were added to a mixture of Cu$_2$O (155 mg, 1.08 mmol), magnesium granule (196 mg, 8.16 mmol) and 2,2'-bipyridine (0.34 g, 2.2 mmol) in dry DMF (20 mL). The mixture was stirred at 85° C. under N$_2$ for 6 h. After removing the solvent in vacuo, the residue was dissolved in minimum CH$_2$Cl$_2$ and next purified with column chromatography (silica gel; hexane/ethyl acetate=4:1) to give compound 3 (1.18 g, 51%) as yellow oil. $^1$H-NMR (CDCl$_3$, 500 MHz) δ 7.95 (s, 1H), 7.49 (dd, 2H, J=8.0, 1.2 Hz), 7.26 (t, 3H, J=8.0 Hz), 1.47 (s, 9H); $^{13}$C-NMR (CDCl$_3$, 125 MHz) δ151.6, 148.6, 145.0, 141.5, 135.8, 135.1, 129.7, 127.7, 127.2, 84.2, 28.3; ESI-MS (C$_{15}$H$_{16}$BrN$_3$O$_2$Se): [M+Na]$^+$ calcd: 451.96, found: 451.91.

5-phenyl-3-(phenylselanyl)pyrazin-2-amine (5)

To a solution of compound 3 (500 mg, 1.17 mmol) in CH$_2$Cl$_2$ (5 mL) was added trifluoroacetic acid (5 mL). After stirring at RT for 30 min, the reaction was diluted with 50 mL CH$_2$Cl$_2$, and neutralized with saturated aq. NaHCO$_3$. The organic layer was isolated, washed twice with saturated aq. NaHCO$_3$ (30 mL) and brine (30 mL), dried over anhydrous Na$_2$SO$_4$, filtered, and concentrated to give the crude compound 4, which was next dissolved in 2 mL EtOH for later use without further purification. In another round-bottom flask, 1,4-bis(diphenylphosphino)butane (BDPB, 30 mg, 0.07 mmol) was added to a suspension of bis(benzonitrile)dichloro palladium (23 mg, 0.06 mmol) in toluene (3 mL), and the mixture was stirred at RT under N$_2$ for 30 min. Next, to the solution of compound 4 in EtOH, phenylboronic acid (172 mg, 1.4 mmol), 1.0 M aq. Na$_2$CO$_3$ (1 mL), toluene (8 mL), and the mixture of BDPB and bis(benzonitrile)dichloro palladium in toluene were added sequentially. The mixture was maintained at reflux under N$_2$ for 12 h. The progress of the reaction was monitored by TLC (hexane/ethyl acetate=2:1). Next, the mixture was cooled down to RT, and the solvent was removed in vacuo. The residue was extracted with ethyl acetate (30 mL), which was washed twice with water (30 mL), dried over anhydrous Na$_2$SO$_4$, and concentrated in vacuo. The residue was next purified with column chromatography (silica gel; gradient elution with hexane/ethyl acetate from 4:1 to 2:1) to give compound 5 (209 mg, 55%). Compound 6 (37 mg, 13%) was also isolated as a by-product. $^1$H-NMR (CDCl$_3$, 500 MHz) δ 8.21 (s, 1H), 7.71 (dd, 2H, J=8.5, 1.5 Hz), 7.61 (dd, 2H, J=7.5, 1.5 Hz), 7.38-7.33 (m, 6H), 5.77 (bs, 2H); $^{13}$C-NMR (CDCl3, 125 MHz) δ 151.2, 143.3, 139.2, 135.7, 134.8, 134.7, 132.61, 129.9, 129.8, 129.0, 126.8, 125.7 ppm; ESI-MS (C$_{16}$H$_{13}$N$_3$Se): [M+H]$^+$ calcd: 328.02; found: 328.05.

Selenoterazine (7):

To a solution of compound 5 (50 mg, 0.153 mmol) and 1,1-diethoxy-3-phenylacetone (51 mg, 0.23 mmol) in degassed EtOH (2 mL) was added 6 N HCl (0.3 mL) under continuous N$_2$ flow. The reaction flask was wrapped in aluminum foil and heated to 80° C. while stirring for 12 h. The mixture was then cooled down to RT. Solvent was removed in vacuo, and the residue was re-dissolved in 1 mL acetonitrile, which was next purified using preparative RP-HPLC (acetonitrile/water=30:70 to 98:2, 2 mL/min, UV 254 nm). Product fractions were combined and lyophilized to give selenoterazine (15.5 mg, 22%), which has to be stored as solid at −80° C. for long-term stability. $^1$H-NMR (DMSO-d$_6$, 500 MHz) δ 7.98 (s, 1H), 7.57 (d, 2H, J=8.5 Hz), 7.41 (d, 2H, J=7.5), 7.35-7.26 (m, 11H), 4.05 (s, 2H); $^{13}$C NMR (DMSO-d$_6$, 125 MHz) δ 139.7, 136.0, 134.2, 132.8, 131.7, 129.3, 129.1, 128.8, 128.5, 128.3, 127.7, 126.0, 114.9, 31.9; ESI-MS (C$_{25}$H$_{19}$N$_3$OSe): [M+H]$^+$ calcd: 458.07, found: 458.08.

2) Method to Synthesize Diphenylterazine (DTZ)

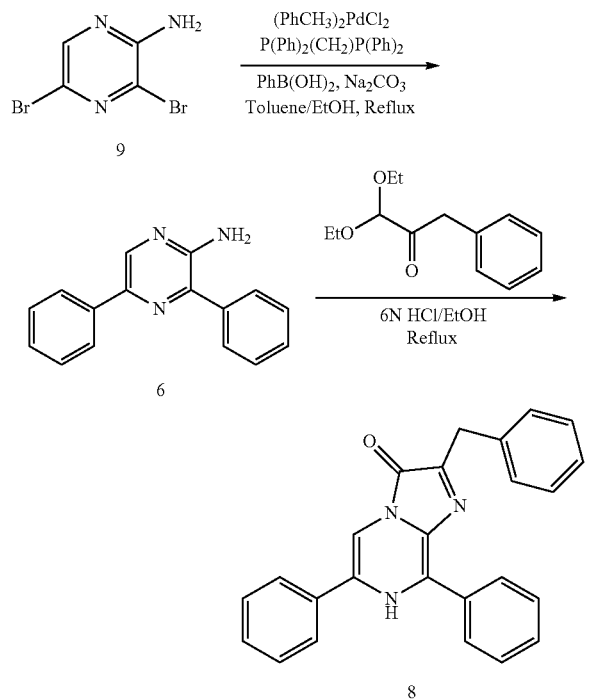

Supplementary Scheme 2. Synthetic Route for Preparing Diphenylterazine as the Major Product.

2-amino-3,5-diphenylpyrazine (6): 1,4-Bis(diphenylphosphino)butane (BDPB, 30 mg, 0.07 mmol) was added to a suspension of bis(benzonitrile)dichloro palladium (23 mg, 0.06 mmol) in toluene (3 mL) and the mixture was stirred at RT for 30 min under N$_2$. To this mixture were sequentially added compound 9 (303 mg, 1.2 mmol) in EtOH (2 mL), phenylboronic acid (318 mg, 2.6 mmol), 1.0 M aq. Na$_2$CO$_3$ (1 mL) and toluene (8 mL). The mixture was heated under reflux for 8 h. After cooling down to RT, the solvent was removed under reduced pressure. The residue was extracted with ethyl acetate (30 mL), which was washed twice with water (30 mL), dried over Na$_2$SO$_4$, and concentrated on a rotary evaporator. The residue was purified with column chromatography (silica gel; gradient elution with hexane/ethyl acetate from 4:1 to 2:1) to give compound 6 (193 mg, 66%). $^1$H NMR (CDCl$_3$) δ 8.55 (s, 1H), 7.95 (d, 2H, J=10.0 Hz), 7.78 (m, 2H), 7.47-7.24 (m, 6H), 5.21 (s, 2H) ppm; HRMS (ESI-TOF) calcd for C$_{16}$H$_{13}$N$_3$ [M+H]$^+$: 248.11, found: m/z 248.12.

diphenylterazine (8): To a solution of compound 6 (50 mg, 0.2 mmol) and 1,1-diethoxy-3-phenylacetone (67 mg, 0.3 mmol) in degassed EtOH (3 mL) was added 6 N HCl (0.3 mL) under continuous N$_2$ flow. The reaction flask was wrapped with aluminum foil and heated at 80° C. with stirring for 6 h. The mixture was cooled down to room temperature, before the solvent was removed in vacuo. The residue was re-dissolved in 1 mL acetonitrile, which was next purified with preparative RP-HPLC (acetonitrile/water=30:70 to 98:2, 2 mL/min, UV 254 nm). Product fractions were combined and lyophilized to give diphenylterazine (26.7 mg, 35%), which has to be stored as solid at −80° C. for long-term stability. $^1$H-NMR (DMSO-d6, 500 MHz) δ 9.54 (s, 1H), 8.16 (d, 2H, J=7.0 Hz), 7.57 (d, 2H, J=7.5 Hz), 7.53 (d, 2H, J=7.0 Hz), 7.33-7.24 (m, 9H), 4.17 (s, 2H) ppm; $^{13}$C NMR (DMSO-d6, 125 MHz) δ 139.9, 136.0, 134.0, 130.5, 130.2, 129.8, 129.3, 128.8, 128.5, 128.3, 128.2, 127.8, 127.3, 126.3, 125.9, 32.0 ppm; HRMS (ESI-TOF) calcd for C$_{25}$H$_{19}$N$_3$O [M−H]$^-$: 376.15, found: m/z 376.14.

The following references relate to this Example and are incorporated by reference herein in their entireties:

1. Jiang, T., Du, L. & Li, M. *Photochem. Photobiol. Sci.* 15, 466-480 (2016).
2. Inouye, S. & Shimomura, O. *Biochem. Biophys. Res. Commun.* 233, 349-353 (1997).
3. Giuliani, G. et al. *Tetrahedron Lett.* 53, 5114-5118 (2012).
4. Yuan, M.-L., Jiang, T.-Y., Du, L.-P. & Li, M.-Y. *Chin. Chem. Lett.* 27, 550-554 (2016).
5. Nishihara, R. et al. *Chem. Commun.* 51, 391-394 (2015).
6. Sun, Y. Q. et al. *Angew. Chem. Int. Ed. Engl.* 51, 7634-7636 (2012).
7. Yamashita, Y., Ono, K., Tomura, M. & Tanaka, S. *Tetrahedron* 53, 10169-10178 (1997).
8. Conley, N. R., Dragulescu-Andrasi, A., Rao, J. & Moerner, W. E. *Angew. Chem. Int. Ed. Engl.* 51, 3350-3353 (2012).
9. Adamczyk, M. et al. *Tetrahedron* 59, 8129-8142 (2003).

Example 3

Materials and General Methods.

Synthetic DNA oligonucleotides were purchased from Integrated DNA Technologies. Restriction endonucleases were purchased from Thermo Scientific Fermentas. Accura high-fidelity DNA polymerase and EconoTaq DNA polymerase were purchased from Lucigen. Products of PCR and restriction digestion were purified by gel electrophoresis and Syd Laboratories Gel Extraction columns. Plasmid DNA was purified using Syd Laboratories Miniprep columns. DNA sequences were analyzed by Retrogen. D-luciferin was purchased from Thermo Fisher Scientific. Coelenterazine was purchased from Gold Biotechnology. Furimazine was purchased from Promega. AkaLumine was purchased from Wako Chemicals USA and acidified with one equivalent of HCl to derive AkaLumine-HCl. All other chemicals were purchased from Sigma-Aldrich, Fisher Scientific, or VWR, and used without further purification. Varian Inova 500 with a 5-mm triple resonance ($^1H/^{13}C/^{15}N$) triple axis gradient probe at the UCR ACIF NMR Facility was used to record all NMR spectra. Chemical shift (δ) is given in parts per million relative to $^1H$ (7.24 ppm) and $^{13}C$ (77.23 ppm) for CDCl3; and $^1H$ (2.50 ppm) and $^{13}C$ (39.5 ppm) for DMSO-d6. Splitting patterns are reported as s (singlet), bs (broad singlet), d (doublet), t (triplet), dd (doublet of doublets), m (multiplet). Coupling constant (J) is given in Hz. ESI-MS was run on an Agilent LC-TOF system by direct infusion. A Gilson PLC 2020 Purification System coupled with an Agela Venusil XBP C18 HPLC Column (10 μM, 100 Å, 10×150 mm) was used for preparative reverse-phase HPLC purifications. BALB/c mice obtained from the Jackson Laboratory (Cat. #000651) were used for in vivo experiments. Animals were maintained in standard conditions and all animal procedures were approved by the UCR Institutional Animal Care and Use Committee.

Construction of plasmids and libraries. Polymerase chain reaction (PCR) was used to amplify all genetic elements using various synthetic oligonucleotide pairs (see Supplementary Table 2).

Supplementary Table 2. Oligonucleotides used in this study.

| Oligo name | Nucleotide sequence |
|---|---|
| XhoI-NL-F | GCAACTCGAGCATGGTCTTCACACTCGAAGATTTCGTTGG (SEQ ID NO: 5) |
| NL-R-HindIII | TTGCCAAGCTTACGCCAGAATGCGTTCGCACAGCCGC (SEQ ID NO: 6) |
| I44I54NNK-F | CCGATCCAAAGGNNKGTCCTGAGCGGTGAAAATGGGCTGAAGNNKGACATCCATGTC (SEQ ID NO: 7) |
| I55I54NNK-R | GACATGGATGTCMNNCTTCAGCCCATTTTCACCGCTCAGGACMNNCCTTTGGATCGG (SEQ ID NO: 8) |
| I138NNK-F | TGGAACGGCAACAAAATTNNKGACGAGCGCCTGATCAAC (SEQ ID NO: 9) |
| I138NNK-R | GTTGATCAGGCGCTCGTCMNNAATTTTGTTGCCGTTCCA (SEQ ID NO: 10) |
| L18D19NNK-F | CAGACAGCCGGCTACAACNNKNNKCAAGTCCTTGAACAGGGAGGTGTG (SEQ ID NO: 11) |
| L18D19NNK-R | CACACCTCCCTGTTCAAGGACTTGMNNMNNGTTGTAGCCGGCTGTCTG (SEQ ID NO: 12) |
| R162C164NNK-R | TTGCCAAGCTTACGCCAGAATGCGTTCMNNCAGMNNCCAGCCGGTCACTCCGTT (SEQ ID NO: 13) |
| HindIII-NL-F-Koz | AATAAAGCTTGCCGCCACCATGGTCTTCACACTCGAAGATTTCGTTGG (SEQ ID NO: 14) |
| NL-R-XhoI | TAATCTCGAGTTACGCCAGAATGCGTTCGCA (SEQ ID NO: 15) |
| NL-R-164R | TAATCTCGAGTTACGCCAGAATGCGTTCATG (SEQ ID NO: 16) |
| NL-R-164S | TAATCTCGAGTTACGCCAGAATGCGTTCACT (SEQ ID NO: 17) |
| FLuc-F | ATTATAAAGCTTGCCGCCACCATGGAAGACGCCAAAAACATAAAGAAAG (SEQ ID NO: 18) |
| FLuc-R | TTATTCTCGAGTTACAATTTGGACTTTCCGCCCTTCTTGG (SEQ ID NO: 19) |
| Ant-HindIII-F-Koz | ATTATAAAGCTTGCCGCCACCATGGTGAGCAAGGGCGAGGAG (SEQ ID NO: 20) |
| Ant-XhoI-R | TTATTCTCGAGTTACTTGTACAGCTCGTCCAT (SEQ ID NO: 21) |
| Te19DtoS_F | GGCTACAACTTGAGTCAAGTCCTTGAA (SEQ ID NO: 22) |
| Te19DtoS_R | TTCAAGGACTTGACTCAAGTTGTAGCC (SEQ ID NO: 23) |
| Te85DtoN_F | TACCCTGTGGATAATCATCACTTTA (SEQ ID NO: 24) |
| Te85DtoN_R | TAAAGTGATGATTATCCACAGGGTA (SEQ ID NO: 25) |
| Te164CtoH_F | TGACCGGCTGGCGTCTGCATGAACGCATTCTGG (SEQ ID NO: 26) |
| Te164CtoH_R | CCAGAATGCGTTCATGCAGACGCCAGCCGGTCA (SEQ ID NO: 27) |
| Antares_F_XhoI | ATAACTCGAGCATGGTGAGCAAGGGCGAGGAG (SEQ ID NO: 28) |
| Antares_R_HindIII | TTGCCAAGCTTACTTGTACAGCTCGTCCAT (SEQ ID NO: 29) |
| NL-Myc-R | TGAGTTTTTGTTCGCCGGAGCCCGCCAGAATGCGTTCGCACAGCCGC (SEQ ID NO: 30) |
| teLuc-Myc-R | TGAGTTTTTGTTCGCCGGAGCCCGCCAGAATGCGTTCATGCAGACGC (SEQ ID NO: 31) |
| yeLuc-Myc-R | TGAGTTTTTGTTCGCCGGAGCCCGCCAGAATGCGTTCACTCAGACGC (SEQ ID NO: 32) |

The gene for NanoLuc was purchased from Integrated DNA Technologies as a gBlock, and further amplified with oligos XhoI-NL-F and NL-R-HindIII. The product was digested with XhoI and HindIII restriction enzymes, and then ligated into a predigested, compatible pBAD/His B plasmid (Life Technologies). To create a gene library with randomization at residues 44, 54, and 138, oligo pairs XhoI-NL-F and I44I54-NNK-R, I44I54-NNK-F and I138-NNK-R, and I138-NNK-F and NL-R-HindIII were utilized to amplify three individual fragments from NanoLuc. The resultant three fragments were purified by agarose gel electrophoresis and utilized as templates for assembly in subsequent PCR reactions by using oligos XhoI-NL-F and NL-R-HindIII. The assembled full-length fragment was subsequently digested with XhoI and HindIII restriction enzymes and ligated into pBAD/His B. To create a library with randomization at residues 18, 19, 162, and 164, a similar multi-step overlap PCR strategy was used. XhoI-NL-F and L18D19-NNK-R, L18D19-NNK-F and R162C164-NNK-R were utilized to create two fragments, which were next assembled by using XhoI-NL-F and NL-R-HindIII. The resultant gene fragment was also treated with XhoI and HindIII, and ligated into a predigested pBAD/His B plasmid. To introduce random mutations across the NanoLuc gene, Taq DNA polymerase was used in all reactions with 0.2 mM $MnCl_2$ added to promote amplification errors. To create mammalian expression plasmids, HindIII-NL-F-Koz and NL-R-XhoI (or NL-R-164H and NL-R-164S) were used to amplify NanoLuc and NanoLuc mutants. The products were treated with HindIII and XhoI restriction enzymes and ligated into a predigested compatible pcDNA3 plasmid (Life Technologies). The Firefly luciferase (FLuc) gene was amplified from a pGL2-GAL4-UAS-Luc plasmid (Addgene Cat #33020) by using FLuc-F and FLuc-R, and inserted into pcDNA3 between HindIII and XhoI sites. Ant-HindIII-F-koz and Ant-XhoI-R were used to amplify a fragment contains Antares gene from pNCS-Antares (Addgene Cat #74279). The product was digested with HindIII and XhoI and then ligated into a predigested pcDNA3 plasmid as mentioned above. To replace the NanoLuc fragment in Antares with teLuc, oligo pairs Ant-HindIII-F-koz and Te19DtoS_R, Te19DtoS_F and Te85DtoN_R, Te85DtoN_F and Te164CtoH_R, Te164CtoH_F and Antares_R_HindIII were utilized to amplify four individual fragments from pNCS-Antares. The resultant four fragments were used as templates and assembled via PCR reactions by using oligo pairs Ant-HindIII-F-koz and Ant-XhoI-R. The product was digested with HindIII and XhoI, purified by agarose gel electrophoresis, and ligated into a predigested pcDNA3 plasmid to give pcDNA3-Antares2. To construct a bacterial expression plasmid for Antares2, oligos Antares_F_XhoI and Antares_R_HindIII were used to amplify the whole gene from pcDNA3-Antares2, which was subsequently digested with XhoI and HindIII and inserted into a compatible, predigested pBAD/HisB plasmid. To construct mammalian expression plasmids with C-terminal Myc tags, the aforementioned forward primers for the construction of pcDNA3 plasmids were individually paired with NL-Myc-R, teLuc-Myc-R, yeLuc-Myc-R, FLuc-Myc-R, or Antares-Myc-R to amplify the corresponding luciferase genes, which were further extended using Myc-R-XhoI paired with the corresponding forward primers. To build bicistronic plasmids containing a self-cleaving porcine teschovirus-1 P2A peptide (GSGATNFSLLKQAGDVEENPGP (SEQ ID NO: 40)), oligos P2A-FLuc-F and FLuc-R were used to amplify the FLuc gene, and teLuc-P2A-R, NLuc-P2A-R, and P2A-ext-R were paired with the corresponding forward primers to amplify teLuc or NanoLuc. These fragments were further assembled using overlap PCR to create NanoLuc-P2A-FLuc or teLuc-P2A-FLuc. The products were digested with HindIII and XhoI, purified by agarose gel electrophoresis, and ligated into a predigested pcDNA3 plasmid. All ligation products were used to transform Escherichia coli DH10B electrocompetent cells, which were next plated on LB agar plates supplemented with ampicillin (100 μg/mL). Additional L-arabinose (0.02%, w/v %) was supplemented to induce protein expression for direct bioluminescence imaging of bacterial colonies.

Library Screening.

DH10B cells containing NanoLuc mutants were plated on LB agar plates supplemented with ampicillin (100 μg/mL) and L-arabinose (0.02%, w/v %) and incubated at 37° C. overnight to form bacterial colonies. Agar plates were left at room temperature for another 6 h, followed by bioluminescence imaging using a luminescence dark box (Stanford Photonics) equipped with a Pixis 1024B CCD camera (Princeton Instruments). Digital images were acquired after spraying ~100 μL of 200 μM substrates to each agar plate, and next processed with the Fiji image analysis software [1] to derive bioluminescence intensities of individual colonies. For each compound, the brightest fifty colonies from a total of ~20,000 colonies were chosen and inoculated in 5 mL liquid LB broth containing ampicillin (100 μg/mL) and L-arabinose (0.02%, w/v %). After overnight growth at 37° C. and 250 rpm, the cultures were moved onto a shaker at room temperature for another 6 h. Cells were next diluted with assay buffer (1 mM CDTA, 0.5% Tergitol NP-40, 0.05% Antifoam 204, 150 mM KCl, 100 mM MES, pH 6.0, 1 mM DTT, and 35 mM thiourea) to $OD_{600}$=0.1. Next, bioluminescence activities of individual samples were measured in white 96-well plates (Costar 3912) on a Synergy Mx Microplate Reader (BioTek) after directly injecting substrates (final concentration of 30 μM). Kinetics were followed for 1-s signal integration every 60 s for a total of 40 min. Mutants showing exceptionally high bioluminescence activities and extended kinetics were chosen for sequencing, protein preparation, and other additional characterization.

Luciferase Expression and Purification.

Figure 18:
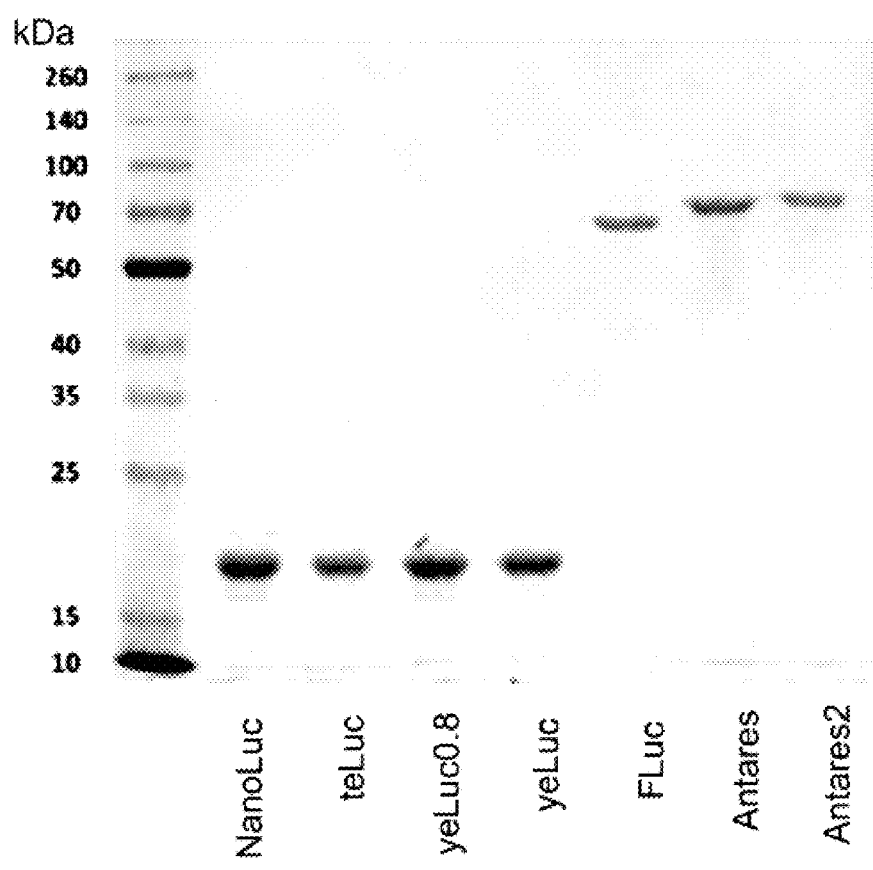
FIG. 18 is an image of SDS-PAGE of purified proteins.

Luciferases were expressed and purified as His6-tagged fusion proteins (FIG. 18). DH10B cells containing corresponding pBAD plasmids were grown in 5 mL LB starter cultures containing ampicillin (100 μg/mL) at 37° C. and 250 rpm overnight. Each saturated overnight culture was diluted 100-fold into 2YT media containing the appropriate antibiotics and grown under the same conditions. When $OD_{600}$ reached 0.7-0.9, the expression culture was induced with L-arabinose (0.2%, w/v %) and incubated at room temperature with shaking at 250 rpm for another 16 h. Cells were harvested by centrifugation at 4700 rpm for 15 min and lysed by sonication. The resulting cell lysate was clarified by centrifugation at 18,000 rpm for 30 min at 4° C. The supernatant was incubated with Ni-NTA agarose beads (Pierce) at 4° C. for 2 h. Agarose beads loaded to a plastic column were sequentially washed with 10 mL of wash buffer 1 (pH 8.0, 50 mM Tris HCl, 20 mM Imidazole, 300 mM NaCl, 1 mM DTT) and 10 mL of wash buffer 2 (pH 8.0, 50 mM Tris HCl, 50 mM Imidazole, 300 mM NaCl, 1 mM DTT), followed by elution with elution buffer (pH 8.0, 50 mM Tris HCl, 300 mM Imidazole, 300 mM NaCl, 1 mM DTT). Proteins were buffer-exchanged into Tris-HCl (50 mM, pH 7.4) containing 1 mM DTT using Thermo Scientific Snakeskin dialysis tubing, and next concentrated using 3-kDa Amicon Ultra Centrifugal Filters (EMD Millipore). Protein concentrations were determined using the Pierce Coomassie Bradford Protein Assay Kit (Thermo Fisher). For storage, glycerol was added to a final concentration of 50% (v/v) and the resultant mixtures were kept at −20° C.

In Vitro Bioluminescence Characterization.

A Synergy Mx Microplate Reader (BioTek) was used for all in vitro bioluminescence characterizations. For kinetics measurements, no emission filter or monochromator was used. 50 μL of luciferin substrates in the assay buffer (1 mM CDTA, 0.5% Tergitol NP-40, 0.05% Antifoam 204, 150 mM KCl, 100 mM IVIES pH 6.0, 1 mM DTT, and 35 mM thiourea) was injected into the wells of white 96-well plates containing 50 μL of pure enzymes in the same assay buffer. The final concentrations of all enzymes and substrates were 100 pM and 30 μM, respectively. Measurements were taken every 60 s post-injection (1-s integration and 10-s shaking during intervals). FLuc bioluminescence assays were performed similarly, except the assay buffer contained 30 mM MOPS, pH 7.0, 1.5 mM ATP, and 5 mM $MgSO_4$. To derive values for apparent Michaelis constants ($K_m$), substrate concentrations varied from 0.78 to 50 μM and peak bioluminescence intensities at individual substrate concentrations were used to fit the Michaelis-Menten equation. To convert relative arbitrary unit (RLU) to the number of photons, the instrument was calibrated by determining the chemiluminescence of 50-800 nM luminol (QY=1.23%) [2] in the presence of 100 nM horseradish peroxidase and 2 mM hydrogen peroxide in 0.1 M $K_2CO_3$ aqueous solution for a total volume of 200 μL. To determine the quantum yields of bioluminescent reactions, 0.01 nmol of each luciferin in 50 μL PBS was injected into 150 μL PBS containing 0.5 nmol of the corresponding luciferase. 1.5 mM ATP and 5 mM Mg were supplemented for the reaction between FLuc and D-luciferin. Signals were integrated until the substrates were completely consumed. Integrated total photos were divided by the total numbers of substrate molecules to derive the quantum yields of bioluminescence reactions. The validation of our results was confirmed by measuring the quantum yields of the *Renilla* luciferase mutant RLuc8 in the presence of CTZ (QY=6.9%) [3] and FLuc in the presence of D-luciferin (QY=41±7.4%) [4]. $k_{cat}$ values for individual enzymes were determined using the equation: $k_{cat}=I_{max}/(QY*[E])$, where $I_{max}$ is the maximal luminescence intensity from the fitting of the Michaelis-Menten equation and [E] is the enzyme concentration. A Tecan M1000 Pro Plate Reader was used to record emission spectra. 50 μL of individual substrates (60 μM) in assay buffers were injected into 50 μL of 2 nM pure enzymes, and the bioluminescence spectra were collected with 0.1-s integration and 1-nm increments from 400 to 750 nm.

Mammalian Cell Culture and Transfection.

HEK 293T (purchased from ATCC and tested for *mycoplasma* by PCR), which is one of the most widely used and readily transfectable cell lines, was used for all tissue culture transfections. HEK 293T cells were cultured at 37° C. with 5% $CO_2$ in Dulbecco's Modified Eagle's Medium (DMEM) supplemented with 10% fetal bovine serum (FBS). Transfection mixtures were prepared with 3 μg of plasmid DNA and 9 μg of PEI (polyethylenimine, linear, MW 25 kDa) in DMEM and incubated for 20 min at room temperature. The medium was first aspirated, and subsequently, the transfection mixtures were added to cells at 70% confluency on 35-mm culture dishes seeded one day prior to transfection. Incubation lasted for 3 h at 37° C. Fresh DMEM containing 10% FBS was next utilized to replace the transfection mixtures. After incubation for another 24 h at 37° C. in a $CO_2$ incubator, the medium was removed and cells were collected and resuspended in Dulbecco's phosphate-buffered saline (DPBS).

Evaluation of the Cytotoxicity of Luciferins.

Cell viability was determined using RealTime-Glo™ MT Cell Viability Assay (Promega) after incubation of HEK 293T cells with individual luciferin substrates for 24 h at 37° C. Cell morphology was further evaluated using microscopy. Briefly, HEK 293T cells in 35-mm culture dishes were washed twice with 400 μL DPBS pre-warmed to 37° C., and further incubated in 500 μL DPBS containing 20 μg/mL propidium iodide (PI), a fluorescent stain for dead cells, at room temperature for 15 min under light-shielded conditions. Cells were further rinsed with pre-warmed 300 μL DPBS three times to remove residual PI. Cells in 300 μL DPBS were next analyzed on a Motic AE31 microscope equipped with a 100 W Short-Arc Mercury lamp, a 540/25 nm excitation filter, a 565 nm longpass dichroic mirror, and a 605/55 nm emission filter.

Bioluminescence Measurements in HEK 293T Cells and Cell Lysates.

The number and density of cells in DPBS suspension were determined using a hemocytometer. Cells were next diluted in DPBS to gain the needed numbers in each 100 μL solution. To use the luminescence dark box to directly image cells, we added luciferase-expressing HEK293T cells (2000 cells per well with ~70% transfection efficiency) and the corresponding luciferin substrates into wells of a white-wall, 96-well plate. Bioluminescence was imaged using a Pixis 1024B cooled CCD camera equipped with a 50-mm f/0.95 lens at one min post-substrate addition. The camera exposure time was 1 s and the field of view was 6×6 inches. A 695BP50 (Omega Optical) filter was utilized to acquire far-red emission. All images were analyzed using the Fiji image analysis software [1]. Cell lysates were prepared by sonication. Without further separation, luciferin substrates in 100 μL assay buffers were added to initiate bioluminescence reactions.

Western Blot.

To examine the expression levels of tested luciferases in mammalian cells, we transfected HEK 293T cells with mammalian expression plasmids harboring C-terminal, c-Myc tagged luciferase genes. Cell lysates were prepared using CelLytic M Cell Lysis Buffer (Sigma-Aldrich) supplemented with cOmplete™ Protease Inhibitor Cocktail (Promega). Cell lysates were clarified by centrifugation at 14,000×g for 10 mins. The Bradford assay was used to determine total protein concentrations in the lysates. 10 μg of total proteins were loaded to each lane and resolved on a 12% SDS-PAGE gel. Proteins were next transferred to a nitrocellulose membrane at 40 V for 3 h. The membrane was blocked with 5% bovine serum albumin (BSA) in 1× phosphate buffered saline with Tween® 20 (PBST) for 1 h, and then incubated with either an anti-c-Myc (Santa Cruz Biotechnology, sc-40; 1:3000 dilution) or an anti-β-actin antibody (ThermoFisher Scientific, PA1-183; 1:10000 dilution) in PBST containing 3% BSA at 4° C. overnight. After washing four times with PBST, the corresponding horseradish peroxidase (HRP) conjugated secondary antibodies (goat anti-mouse IgG, ThermoFisher Scientific, 31430; or goat anti-rabbit IgG, Sigma-Aldrich, A0545; both at 1:10000 dilution) were added and incubated for 1 h at room temperature. Membranes were visualized with Amersham ECL Western Blotting Detection Reagent (GE Healthcare) on a Bio-Rad Gel Doc XR System.

Bioluminescence Imaging of HEK 293T Cells at Superficial Sites on Live Mice.

BALB/c mice on a 37° C. electronic heat pad were anesthetized using 2% isoflurane in 100% oxygen with a flow of 0.5 L/min. We subcutaneously injected 2 million HEK 293T cells transfected with luciferase genes and resuspended in 100 μL PBS near the right, dorsolateral trapezius region of unshaved BALB/c mice; and another 2 million cells transfected with an empty vehicle vector and also resuspended in 100 μL PBS to the left, dorsolateral thoracolumbar region. After cells were settled for 5 min, the corresponding luciferase substrates with indicated concentrations in 100 µL PBS were also subcutaneously injected to each site. Mice were subsequently imaged with a 30-s exposure per frame for a total of 5 min using a luminescence dark box (Stanford Photonics) equipped with a Pixis 1024B cooled CCD camera. The Fiji image analysis software [1] was used to analyze images and integrate bioluminescence intensities over common regions of interest encompassing all injected cells.

Bioluminescence Imaging in Deep Tissues of Live Mice.

Hydrodynamic transfections were performed on BALB/c mice as described elsewhere [5]. Briefly, 20 µg of each luciferase-expressing plasmid in sterilized saline (volume equivalent to 9% bodyweight of the treated mouse) was injected into restrained mice via the tail vein over 4-8 sec. Mice were allowed to recover on heat pads and were monitored until their breathing rate returned to normal. Bioluminescence images were acquired at 12 h post-injection. D-luciferin or AkaLumine-HCl at the indicated dose was dissolved in 100 µL PBS and intraperitoneally injected into FLuc-transfected mice. Prior to intraperitoneal injections of CTZ analogs to teLuc, Antares, or Antares2 transfected mice, the indicated dose of DTZ or furimazine was dissolved in a 100 µL solution containing 8% glycerol, 10% ethanol, 10% hydroxypropyl-β-cyclodextrin, and 35% PEG 400 in water. To inject 3.3 µmol DTZ or furimazine, the total volumes were increased to 500 µL. The luminescence dark box (Stanford Photonics) equipped with a Pixis 1024B cooled CCD camera was again used to image anesthetized mice with a 1-min exposure per frame over a course of 10 min. The Fiji image analysis software [1] was used to process images and derive integrated intensities.

Bioluminescence Imaging of Intravenously Injected HEK 293T Cells.

At 48 h after transfection, one million HEK 293T cells expressing luciferases were trypsinized, pelleted, and resuspended in 100 µL PBS. Cells expressing teLuc, Antares, or Antares2 were combined with the same number of cells expressing FLuc and injected into the tail vein of BALB/c mice placed in a restrainer. Mice were recovered for 5 h, anaesthetized, intraperitoneally injected with 3.3 µmol D-luciferin, and immediately imaged with a 1-min exposure per frame over a course of 20 min. Mice were kept under isoflurane anesthesia on a heat pad during imaging. After the diminishing of the FLuc bioluminescence, 0.3 µmol DTZ or furimazine was intraperitoneally injected. Again, mice were imaged with a 1-min exposure per frame over a course of 20 min. The images were processed using the Fiji image analysis software [1] and the frames with highest signals in individual experiments were used for comparison.

Statistical Analysis.

Unpaired two-tailed t-tests were used to determine all P values. No statistical methods were used to pre-determine the sample size. No sample was excluded from data analysis, and no blinding was employed. Animals were randomly assigned to receive various treatments. Unless otherwise indicated, data are shown as mean±s.d., and error bars in figures represent s.d.

The following references relate to this Example and are incorporated by reference herein in their entireties:
1. Schindelin, J. et al. *Nat. Methods* 9, 676-682 (2012).
2. Ando, Y. et al. *Photochem. Photobiol.* 83, 1205-1210 (2007).
3. Loening, A. M., Dragulescu-Andrasi, A. & Gambhir, S. S. *Nat. Methods* 7, 5-6 (2010).
4. Ando, Y. et al. *Nat Photon* 2, 44-47 (2008).
5. Liu, F., Song, Y. & Liu, D. *Gene Ther.* 6, 1258-1266 (1999).

REFERENCES

The following references relate to the entire application and are incorporated by reference herein in their entireties:
1. Negrin, R. S. & Contag, C. H. *Nat. Rev. Immunol.* 6, 484-490 (2006).
2. Arranz, A. & Ripoll, J. *Frontiers in pharmacology* 6, 189 (2015).
3. Inglese, J. et al. *Nat. Chem. Biol.* 3, 466-479 (2007).
4. Saito, K. et al. *Nat. Commun.* 3, 1262 (2012).
5. Hall, M. P. et al. *ACS Chem. Biol.* 7, 1848-1857 (2012).
6. Stacer, A. C. et al. *Mol. Imaging* 12, 1-13 (2013).
7. Adams, S. T., Jr. & Miller, S. C. *Curr. Opin. Chem. Biol.* 21c, 112-120 (2014).
8. Evans, M. S. et al. *Nat. Methods* 11, 393-395 (2014).
9. Kuchimaru, T. et al. *Nat. Commun.* 7, 11856 (2016).
10. Inouye, S. & Shimomura, O. *Biochem. Biophys. Res. Commun.* 233, 349-353 (1997).
11. Wu, C., Nakamura, H., Murai, A. & Shimomura, O. *Tetrahedron Lett.* 42, 2997-3000 (2001).
12. Inouye, S. et al. *Biochem. Biophys. Res. Commun.* 437, 23-28 (2013).
13. Jiang, T., Du, L. & Li, M. *Photochem. Photobiol. Sci.* 15, 466-480 (2016).
14. Nishihara, R. et al. *Chem. Commun.* 51, 391-394 (2015).
15. Inouye, S., Sato, J., Sahara-Miura, Y., Yoshida, S. & Hosoya, T. *Biochem. Biophys. Res. Commun.* 445, 157-162 (2014).
16. Tomabechi, Y. et al. *Biochem. Biophys. Res. Commun.* 470, 88-93 (2016).
17. Chu, J. et al. *Nat. Biotechnol.* 34, 760-767 (2016).
18. Suzuki, K. et al. *Nat. Commun.* 7, 13718 (2016).
19. Dixon, A. S. et al. *ACS Chem. Biol.* 11, 400-408 (2016).
20. Yang, J. et al. *Nat. Commun.* 7, 13268 (2016).
21. Inouye, S. et al., FEBS Lett. 2000 Sep. 8; 481(1):19-25.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A bioluminescent protein, comprising a substituted luciferase polypeptide comprising the amino acid sequence set forth in SEQ ID NO: 1 with amino acid substitutions at positions corresponding to positions 21 and 166 of SEQ ID NO: 1, and comprising one or more amino acid substitutions at one or more positions corresponding to positions 3, 16, 20, 29, 30, 71, 87, 114, and 144 of SEQ ID NO: 1.

2. The bioluminescent protein of claim 1, wherein the luciferase polypeptide is substituted at positions corresponding to position 87, positions 20 and 30, or positions 3, 16, 20, 29, 30, 71, 114, and 144, of SEQ ID NO: 1.

3. The bioluminescent protein of claim 1, wherein the luciferase polypeptide comprises SEQ ID NO: 2, 3 or 4.

4. The bioluminescent protein of claim 1, further comprising a fluorescent protein connected to the substituted luciferase polypeptide.

5. The bioluminescent protein of claim 4, wherein one copy of the fluorescent protein is fused to the N-terminus of the substituted luciferase polypeptide, and another copy of the fluorescent protein is fused to the C-terminus of the substituted luciferase polypeptide.

6. The bioluminescent protein of claim 4, wherein the fluorescent protein is connected to the substituted luciferase polypeptide so as to allow bioluminescence resonant energy transfer (BRET) between the substituted luciferase polypeptide and the fluorescent protein.

7. The bioluminescent protein of claim 4, wherein the substituted luciferase polypeptide comprises the amino acid sequence of SEQ ID NO: 2, 3 or 4.

8. A method of preparing an analog of 6-(4-hydroxyphenyl)-2-[(4-hydroxyphenyl)methyl]-8-(phenylmethyl)-7H-imidazo[1,2-a]pyrazin-3-one (coelenterazine), wherein coelenterazine comprises an imidazopyrazine backbone, the method comprising including a selenium-containing group at position C8 of the imidazopyrazine backbone, the method being carried out according to the following Scheme I

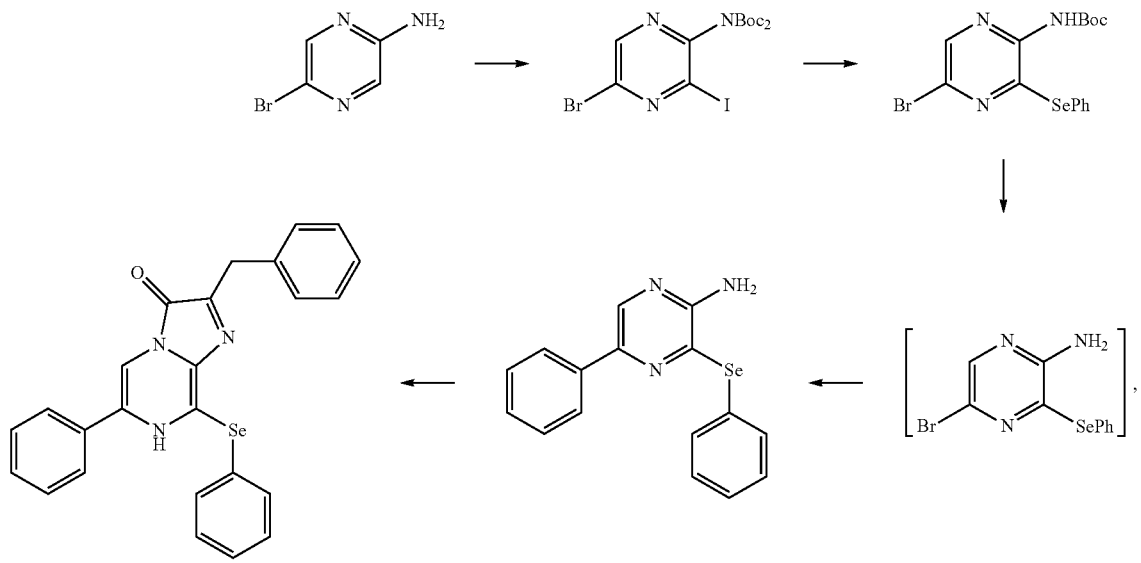

Scheme 1 wherein the method comprises reacting 2-amino-5-bromopyrazine with N-iodosuccinimide to produce a reaction product, and reacting the reaction product with di-tert-butyl dicarbonate to produce di-tert-butyl (5-bromo-3-iodopyrazin-2-yl) carbamate;

reacting the di-tert-butyl (5-bromo-3-iodopyrazin-2-yl) carbamate with diphenyl diselenide to produce tert-butyl (5-bromo-3-(phenylselanyl)pyrazin-2-yl)carbamate;

removing the Boc group from the tert-butyl (5-bromo-3-(phenylselanyl)pyrazin-2-yl)carbamate to give compound 5-bromo-3-(phenylselanyl)pyrazin-2-amine, and then substituting a phenyl group for the bromo group of 5-bromo-3-(phenylselanyl)pyrazin-2-amine to produce 5-phenyl-3-(phenylselanyl) pyrazin-2-amine; and reacting the 5-phenyl-3-(phenylselanyl)pyrazin-2-amine with 1,1-diethoxy-3-phenylacetone to produce the analog.

9. A combination comprising a bioluminescent protein of claim 1 and a luciferin.

10. The combination of claim 9, wherein the substituted luciferase polypeptide of the bioluminescent protein comprises the amino acid sequence of SEQ ID NO: 2, 3 or 4.

11. The combination of claim 10, wherein the luciferin is one or a combination of the following compounds:

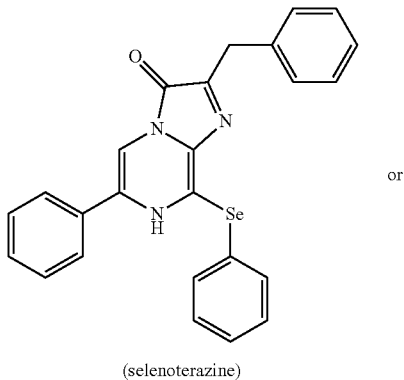

(selenoterazine)

or

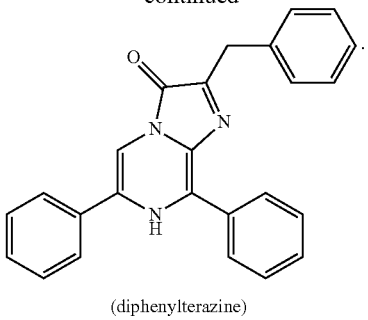

(diphenylterazine)

12. A nucleic acid encoding the bioluminescent protein of claim 1.

13. A vector encoding the nucleic acid of claim 12.

14. An expression vector encoding the nucleic acid of claim 12 functionally connected to a promoter.

15. A cell line containing the expression vector of claim 14 and expressing the bioluminescent protein.

16. A method of producing luminescence, comprising reacting a luciferin with the bioluminescent protein of claim 1.

17. The method of claim 16, wherein the substituted luciferase polypeptide of the bioluminescent protein comprises the amino acid sequence of SEQ ID NO: 2, 3 or 4.

18. The method of claim 17, wherein the luciferin is selenoterazine and/or diphenylterazine.

19. The method of claim 16, wherein the bioluminescent protein further comprises a fluorescent protein connected to the substituted luciferase polypeptide so as to allow BRET activity between the substituted luciferase polypeptide and the fluorescent protein.

20. A non-human cell transfected with the expression vector of claim 14 and expressing the bioluminescent protein.

* * * * *